(12) United States Patent
MacGabann

(10) Patent No.: US 10,595,183 B2
(45) Date of Patent: Mar. 17, 2020

(54) EMERGENCY RESPONSE SYSTEM

(71) Applicant: MosSmith Industries, Inc., San Diego, CA (US)

(72) Inventor: Padraig MacGabann, Coronado, CA (US)

(73) Assignee: MosSmith Industries, Inc., San Diego, CA (US)

( * ) Notice: Subject to any disclaimer, the term of this patent is extended or adjusted under 35 U.S.C. 154(b) by 0 days.

(21) Appl. No.: 16/377,040

(22) Filed: Apr. 5, 2019

(65) Prior Publication Data

US 2019/0313230 A1    Oct. 10, 2019

Related U.S. Application Data

(60) Provisional application No. 62/653,856, filed on Apr. 6, 2018.

(51) Int. Cl.
*H04W 4/90* (2018.01)
*H04W 4/029* (2018.01)
(Continued)

(52) U.S. Cl.
CPC ............ *H04W 4/90* (2018.02); *G06N 20/00* (2019.01); *G06Q 10/06316* (2013.01);
(Continued)

(58) Field of Classification Search
CPC ........ H04W 4/90; H04W 4/029; G06N 20/00; H04M 1/72536; G06Q 10/06316
See application file for complete search history.

(56) References Cited

U.S. PATENT DOCUMENTS 9,595,184 B2    3/2017    Almansour
9,683,856 B2 *  6/2017    Iyer .................... G01C 21/3415
(Continued)

FOREIGN PATENT DOCUMENTS

EP    2219163 A1    8/2010
EP    2710818 B1    9/2015
(Continued)

OTHER PUBLICATIONS

Hugo Paredes, Benjamim Fonseca, Miriam Cabo, Tania Pereira, and Filipe Fernandes. SOSPhone: a mobile application for emergency calls, Journal of Universal Access in the Information Society, Aug. 2014.
(Continued)

*Primary Examiner* — Muthuswamy G Manoharan
(74) *Attorney, Agent, or Firm* — Knobbe, Martens, Olson & Bear, LLP

(57) ABSTRACT

Generally described, one or more aspects of the present application correspond to distributed computing systems for coordinating emergency rescue operations. The disclosed distributed emergency response system includes a mobile rescue application that increases the efficiency and reliability of users submitting rescue requests, a server-based application that coordinates dispatches in response to incoming rescue requests, and a mobile responder application that provides more efficient rescue through real-time location updates received from the mobile rescue application. The rescue application can include a dynamic, menu-based user interface to quickly solicit the emergency information needed for automated triage and dispatch.

20 Claims, 22 Drawing Sheets

(51) Int. Cl.
*H04W 4/02* (2018.01)
*H04M 3/51* (2006.01)
*H04M 1/00* (2006.01)
*G06Q 10/06* (2012.01)
*G06N 20/00* (2019.01)
*H04M 1/725* (2006.01)

(52) U.S. Cl.
CPC ..... *H04M 1/72536* (2013.01); *H04M 3/5116* (2013.01); *H04W 4/023* (2013.01); *H04W 4/029* (2018.02); *H04M 2242/04* (2013.01)

(56) References Cited

U.S. PATENT DOCUMENTS

| | | | |
|---|---|---|---|
| 10,003,945 B2 | 6/2018 | Papakonstantinou | |
| 2012/0136923 A1* | 5/2012 | Grube | H04W 4/90 709/203 |
| 2014/0333412 A1* | 11/2014 | Lewis | G07C 9/00031 340/5.2 |
| 2015/0004926 A1* | 1/2015 | AlHazme | H04M 1/72541 455/404.2 |
| 2015/0084757 A1 | 3/2015 | Annibale et al. | |
| 2015/0111524 A1* | 4/2015 | South | H04W 4/90 455/404.2 |
| 2015/0289122 A1* | 10/2015 | Friesen | H04W 4/02 455/404.2 |
| 2015/0317809 A1 | 11/2015 | Chellappan | |
| 2015/0365246 A1 | 12/2015 | Kane | |
| 2017/0024088 A1 | 1/2017 | La Pean et al. | |
| 2017/0034682 A1* | 2/2017 | Matsumasa | G06Q 10/06 |
| 2017/0105108 A1 | 4/2017 | South | |
| 2017/0372594 A1 | 12/2017 | Paulin | |
| 2018/0262897 A1* | 9/2018 | Hennessy | H04W 4/02 |
| 2018/0365942 A1* | 12/2018 | Molloy | G08B 7/066 |

FOREIGN PATENT DOCUMENTS

| | | |
|---|---|---|
| WO | WO2014096920 A1 | 6/2014 |
| WO | WO2014124497 A1 | 8/2014 |
| WO | WO2016149072 A1 | 9/2016 |
| WO | WO2017008861 A1 | 1/2017 |
| WO | WO2017196753 A1 | 11/2017 |

OTHER PUBLICATIONS

Glen L. Urban and Fareena Sultan. The Case for 'Benevolent' Mobile Apps. MIT Sloan Management Review. Winter 2015.
Facilitating the Deployment of Text-to-911 and Other Next Generation 911 Applications; Framework for Next Generation 911 Deployment. The Federal Register. Oct. 12, 2011.
Ruicong Han, Xuefeng Zhao, Yan Yu, Quanhua Guan, Deli Peng, Mingchu Li, and Jinping Ou. Emergency Communication and Quick Seismic Damage Investigation Based on Smartphone. Advances in Materials Science and Engineering. Sep. 2016.
Cranmore, Mark. Orchestrating Future Mission Critical Dispatch. Law and Order. Apr. 2014.
Banse, Tom. Smartphone App Alerts Trained Bystanders to Cardiac Emergencies. Voice of America News. Jul. 1, 2015.
Gavigan, Jennifer. Software First Responder. Law and Order. Apr. 2012.
Gavigan, Jennifer. State-of-the-Art Police Agency: Software. Law and Order. Nov. 2008.
Teija Norri-Sederholm, Minna Joensuu, and Aki-Mauri Huhtinen. Ensuring Information Flow and the Situation Picture in Public Safety Organisations' Situation Centres. International Journal of Cyber Warfare and Terrorism. Jan. 2018.
Stephane Roche, Eliane Propeck-Zimmermann, and Boris Mericskay. GeoWeb and crisis management: issues and perspectives of volunteered geographic information. GeoJournal. Feb. 2013.

* cited by examiner

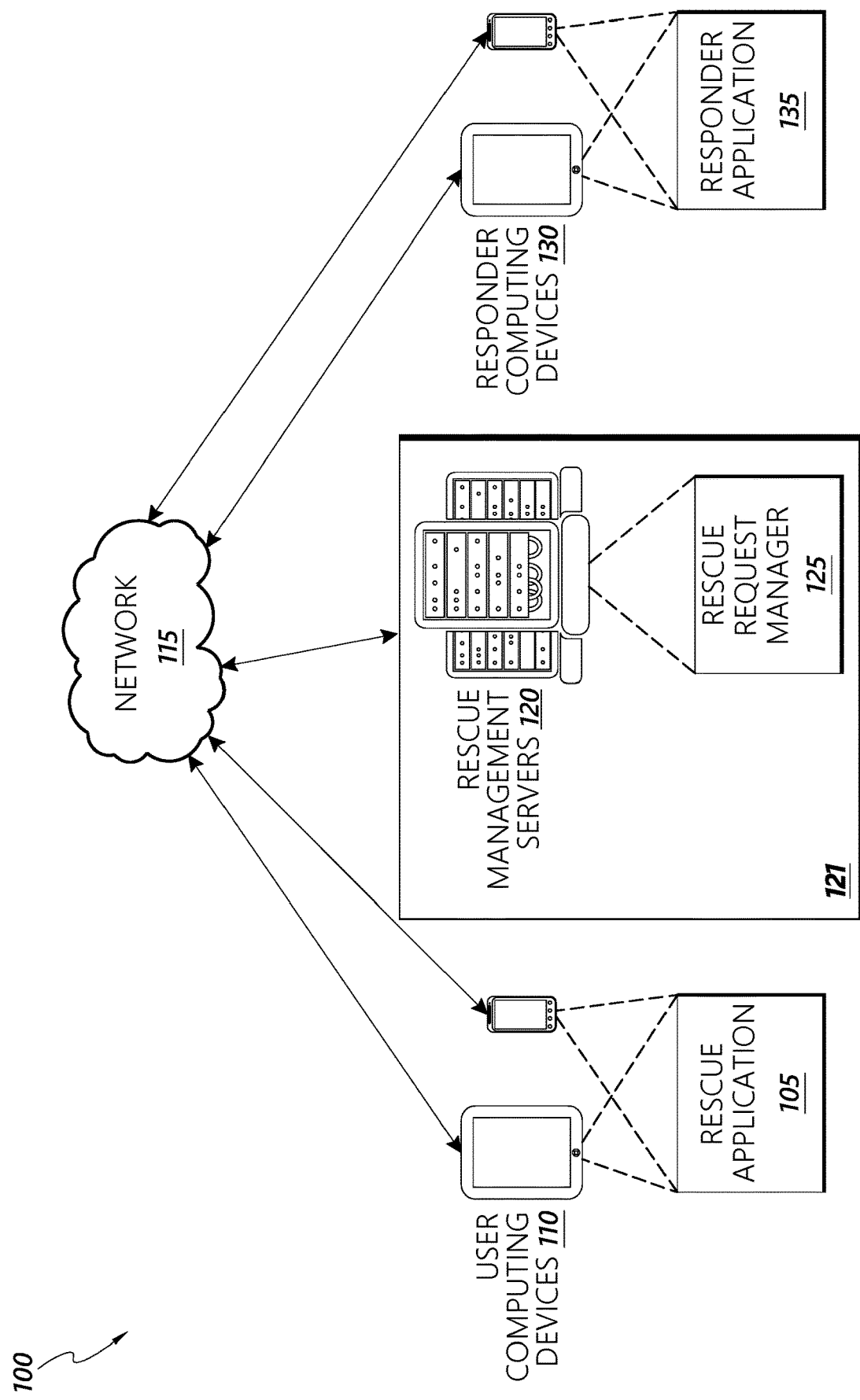

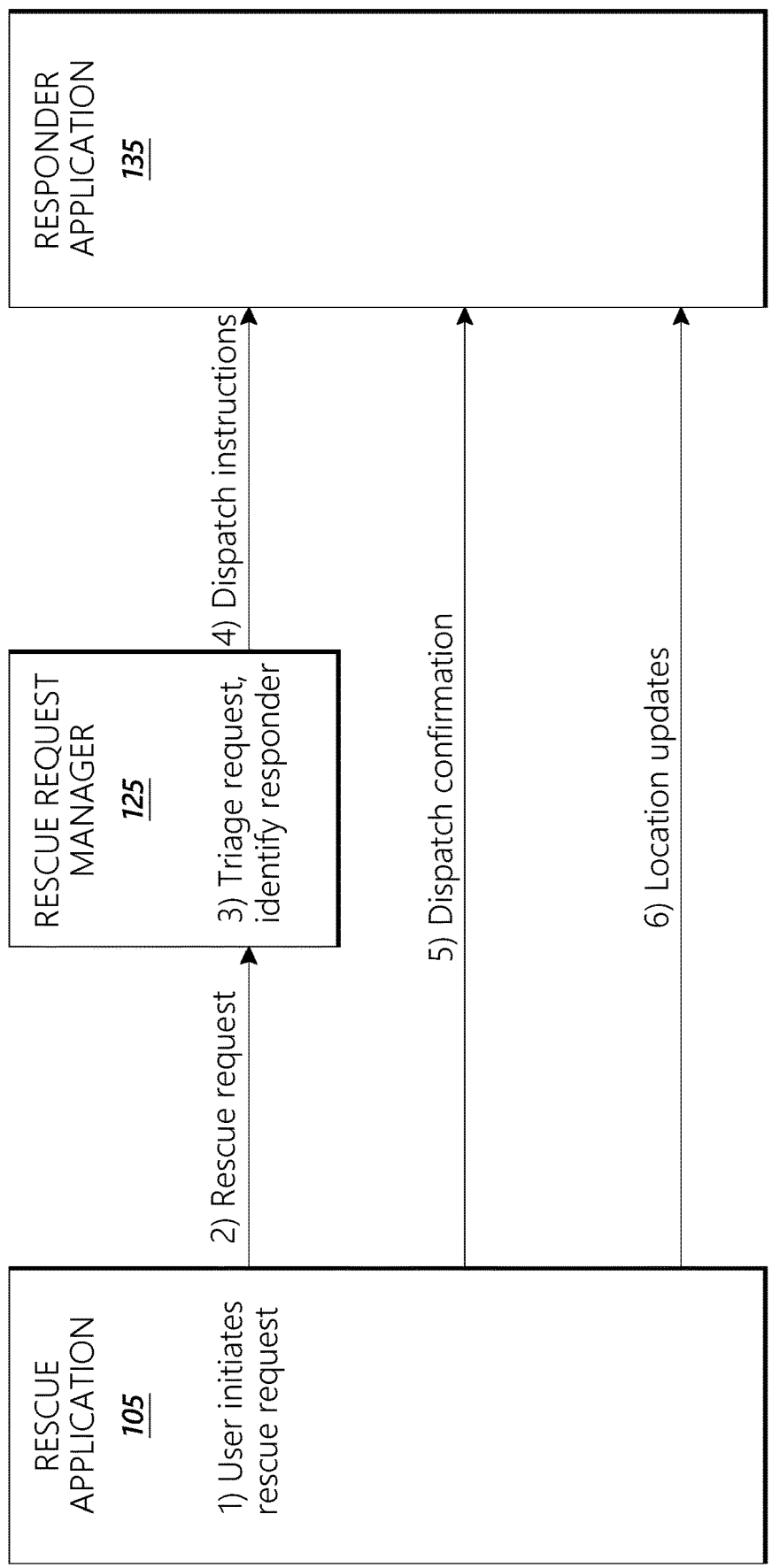

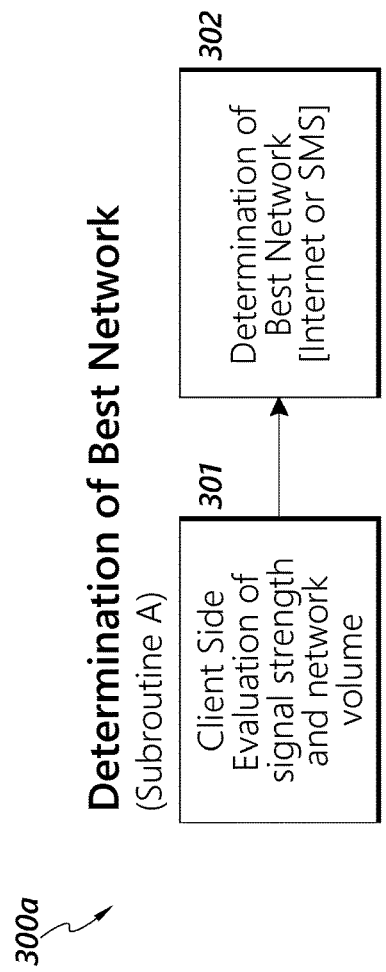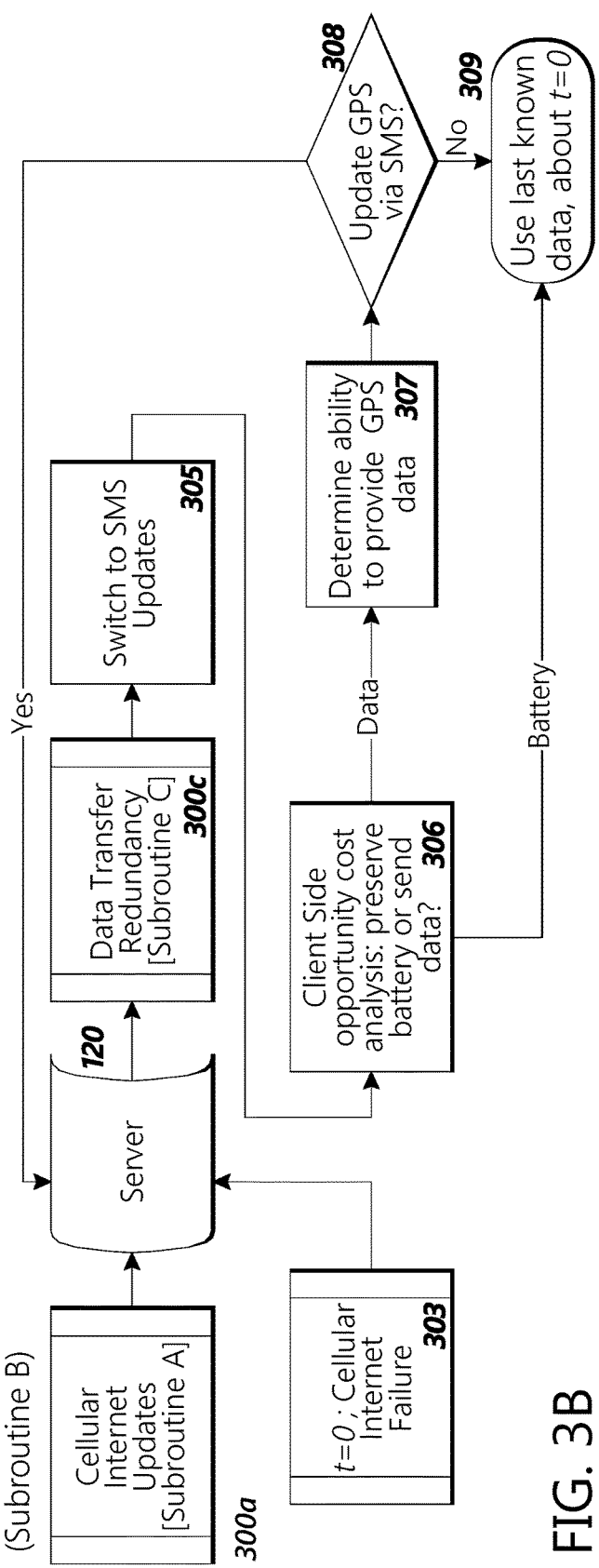
FIG. 3A
FIG. 3B

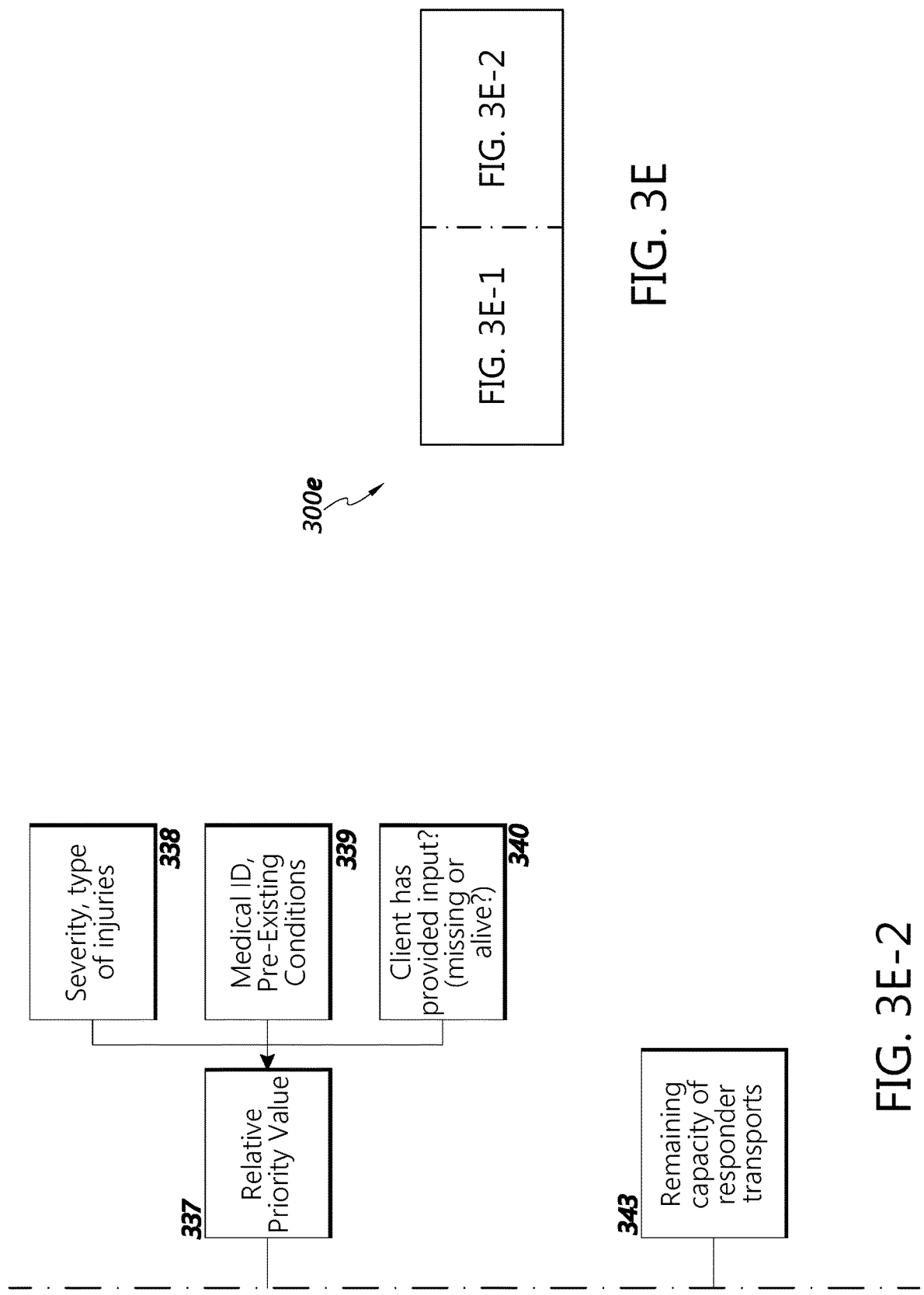

EMERGENCY RESPONSE SYSTEM

CROSS-REFERENCE TO RELATED APPLICATIONS

This application claims benefit of priority to U.S. Provisional Application No. 62/653,856, filed Apr. 6, 2018 and titled "EMERGENCY RESPONSE SYSTEM", the content of which is hereby incorporated by reference in its entirety.

FIELD

The present application relates generally to emergency response systems, and management thereof, and more particularly to wireless emergency systems including an emergency mobile application that sends rescue requests to 9-1-1 or other emergency response numbers or services.

BACKGROUND

Emergency telephone numbers, for example 9-1-1 in parts of North America, can be used in emergency circumstances to request dispatch of emergency responders. Typically, dialing an emergency telephone number will link a caller to an emergency dispatch office, referred to as a public-safety answering point ("P SAP"), which will coordinate the dispatch of emergency responders (e.g., police officers, fire fighters, emergency medical personnel) to the caller's location. Response times and routes can vary based on factors such as volume of emergency callers, availability of emergency responders, and environmental factors.

SUMMARY

The systems, methods and devices of this disclosure each have several innovative aspects, no single one of which is solely responsible for the desirable attributes disclosed herein.

One aspect relates to an emergency response system. The emergency response system comprises a first computing device comprising one or more first processors programmed to execute instructions that cause at least one first processor of the one or more first processors to generate a first rescue request packet based on emergency information provided by a user. The emergency response system also comprises at least one server comprising one or more second processors programmed to execute instructions that cause at least one second processor of the one or more second processors to receive a plurality of rescue request packets from a plurality of computer devices, including the first rescue request packet from the first computing device, identify a rescue request from each of the plurality of rescue request packets, the rescue request providing details regarding a respective victim and respective emergency conditions based on the emergency information, triage the rescue requests to identify an order in which the respective victims are to be rescued, identify an emergency responder to dispatch to each respective victim based at least in part on the triaging of the rescue requests, and coordinate dispatch of the emergency responder based on the emergency information. The emergency response system further comprises a second computing device comprising one or more third processors programmed to execute instructions that cause at least one third processor of the one or more third processors to receive dispatch instructions from the at least one server, the dispatch instructions including the emergency information and a location of the first computing device.

Another aspect relates to a computer-implemented method, comprising receiving a plurality of rescue request packets from a plurality of computer devices, including a first rescue request packet based on emergency information provided by a user from a first computing device; identifying a rescue request from each of the plurality of rescue request packets, the rescue request providing details regarding a respective victim and respective emergency conditions based on the emergency information; triaging the rescue requests to identify an order in which the respective victims are to be rescued; identifying an emergency responder to dispatch to each respective victim based at least in part on the triaging of the rescue requests; coordinating dispatch of the emergency responder based on the emergency information; and transmitting dispatch instructions to the emergency responder, the dispatch instructions including the emergency information and a location of the first computing device.

Another aspect relates to a non-transitory, computer-readable storage media storing computer-executable instructions that, when executed by a computer system, configure the computer system to perform operations comprising receiving a plurality of rescue request packets from a plurality of computer devices, including a first rescue request packet based on emergency information provided by a user from a first computing device; identifying a rescue request from each of the plurality of rescue request packets, the rescue request providing details regarding a respective victim and respective emergency conditions based on the emergency information; triaging the rescue requests to identify an order in which the respective victims are to be rescued; identifying an emergency responder to dispatch to each respective victim based at least in part on the triaging of the rescue requests; coordinating dispatch of the emergency responder based on the emergency information; and transmitting dispatch instructions to the emergency responder, the dispatch instructions including the emergency information and a location of the first computing device.

BRIEF DESCRIPTION OF THE DRAWINGS

The disclosed aspects will hereinafter be described in conjunction with the appended drawings and appendices, provided to illustrate and not to limit the disclosed aspects, wherein like designations denote like elements.

FIG. 1A depicts a schematic diagram of an emergency response system in which various embodiments according to the present disclosure can be implemented.

FIG. 1B depicts example interactions between the rescue application, rescue request manager, and responder application of FIG. 1A, according to the present disclosure.

FIG. 3A is a flowchart of an example process for a determination of best network subroutine of FIG. 2C.

FIG. 3B is a flowchart of an example process for an emergency location update protocol subroutine of FIG. 2C.

FIG. 3E shows how FIGS. 3E-1 and 3E-2 are related to one another; FIGS. 3E-1 and 3E-2 are a flowchart of an example process for a triage algorithm subroutine of FIG. 2C.

DETAILED DESCRIPTION

Figure 2A:
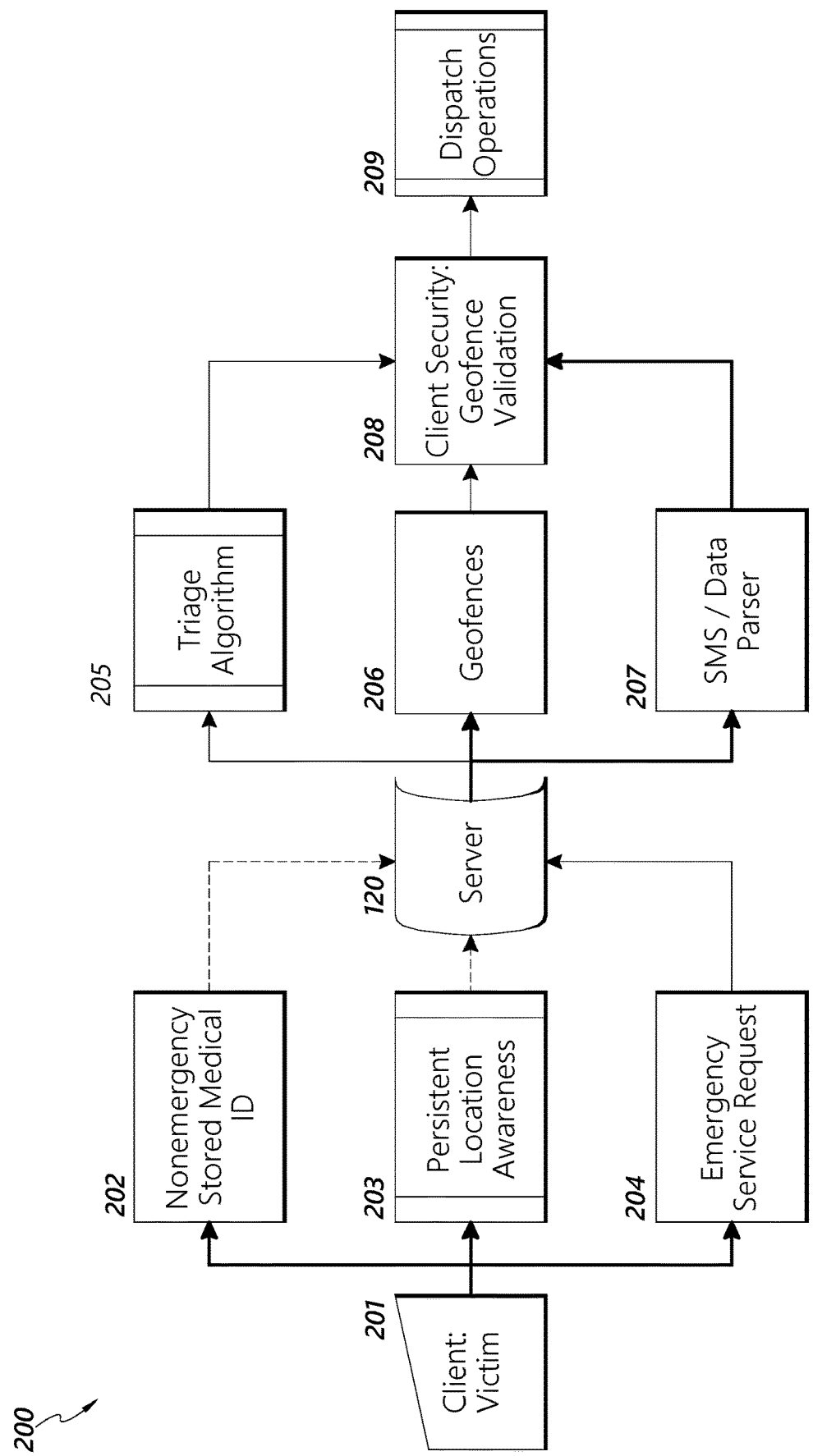
FIG. 2A is a flowchart of an example process for emergency rescue requests and dispatch operations within the emergency response system of FIG. 1A.

Generally described, the present disclosure relates to a distributed emergency response computing system and management thereof, the distributed emergency response computing system including, in at least some embodiments, a mobile rescue application that operates on an emergency response requesting user's device and increases the efficiency and reliability of user-submitted rescue requests, a server-based rescue request manager application that coordinates dispatches in response to incoming rescue requests, and a mobile responder application that operates in conjunction with dispatch parties (for example, including dispatch services of emergency responders and the emergency responders) and provides the dispatch entities with real-time location updates received from the mobile rescue application. Typically, a person in need of emergency assistance calls 9-1-1 (or another emergency telephone number) and explains the nature of their emergency to a PSAP agent in order to have emergency responders dispatched. However, such conventional emergency response systems suffer from several drawbacks that can negatively impact the likelihood that the caller will be rescued.

For example, some 9-1-1 callers may be panicked due to experiencing an emergency situation. Further, some emergency situations (for example, where the caller is hiding from an assailant) may limit the ability of the caller to speak to the PSAP agent, as such speaking may risk the caller being overheard and may place the caller in danger. Other scenarios (for example, choking, a loud environment) may limit the ability of the caller to speak at all or to convey any information through speech. In addition, communication networks (for example, the Internet, landlines, mobile calling networks) may fail during natural and/or manmade disasters (for example, hurricanes, earthquakes, fires, flooding, sabotage, and so forth). These scenarios can create difficulties and inefficiencies for the PSAP agent to obtain the information needed from the caller to dispatch the appropriate emergency responder. Some systems or locales offer text to 9-1-1 services; however, these services are only available in certain locations and, when available, typically require the user (for example, the texter) to manually type in the details of their emergency using a text message interface. If insufficient information is provided with the initial text message, additional time and communications are required for the PSAP agent to obtain the needed information from the user before dispatching the appropriate emergency responder. Further, although once the caller or texter disengages from the PSAP agent, any changes in their location may not be communicated to the emergency responder. These scenarios, alone and in combination, can hinder the effective rescue of persons in emergency situations.

The disclosed technology addresses the aforementioned challenges, among others, (1) by providing users with a dynamic and intuitive user interface (via the mobile rescue application) that enables them to quickly select options that pertain to their particular emergency, (2) by implementing automated triaging and dispatching at a centralized rescue management system (that operates the rescue request manager), and (3) by providing emergency responders (and responder dispatchers) with a responder application that provides location updates received from the rescue application during dispatch. Additionally, the rescue application can dynamically select from available communications networks to compensate for network outages.

With respect to the rescue application, the user can initially be presented with a menu asking them to select from a number of general categories of emergency. These categories may be dynamically modified and/or reordered based on real-time disaster monitoring (e.g., known earthquake or flood locations, predicted fire trajectories). The rescue application can then show the user one or more follow-up user interfaces to obtain more specific information regarding the severity and details of the emergency, with these follow-up user interfaces selected dynamically by the rescue application based on the initial user selection indicating which type of emergency the user is experiencing. This dynamic, menu-based approach can make text-to-911 and other communications with the emergency response system more efficient by quickly obtaining all required information for the dispatch of appropriate emergency responders and using this information to generate a rescue request packet for transmission, for example by the rescue application. In addition, the rescue application may allow users to establish a user profile or otherwise pre-enter certain relevant medical information (for example, current medical conditions, medications, allergies, blood type) that can be automatically included in the rescue request packet, thereby saving user time and effort during the emergency. Further, the rescue application can provide for automated emergency dispatch and location tracking even during internet or landline failure by adaptively determining whether to send rescue request packets over Internet, Short Message Service ("SMS"), or other communications medium. SMS is a text messaging service component of mobile device systems that uses standardized communication protocols to enable mobile devices to exchange short text messages.

With respect to the server-based rescue request manager application, automated triaging and dispatching for a high volume of rescue requests, such as during a natural disaster or other large-scale emergency, may increase the number of disaster victims that can be rescued in a given period of time and by a limited number of emergency responders. Beneficially, the rescue request manager can quickly perform automated triaging to identify which victims require rescue most urgently, and can match those victims with appropriate emergency responders as well as send dispatch instructions to the respective emergency responders. Time is precious in a disaster, so automating various aspects of the rescue request and responder dispatch process(es) can beneficially save many lives.

Beneficially, the responder application enables dispatched emergency responders to receive critical information in real time. This can include updated location of the victim, updated dispatch routing information, and updated status information regarding the victim (for example, if the victim's injuries have changed or if their emergency situation has escalated or de-escalated). In addition, the responder application can allow the user to receive updates regarding the status and location of the dispatched emergency responder, by communication between the responder application and the rescue application.

As would be appreciated by one of skill in the art, the use of the distributed emergency response system to enable rescue of victims, as disclosed herein, represents a significant technological advance over prior implementations. Specifically, the dynamic rescue application user interface enables users to efficiently and quickly provide a complete emergency situation information packet that enables prioritization of their request and/or matching of the user with an emergency responder. As well, the persistent communication between the rescue application and the responder application provides for real-time location tracking of victims by personnel of the emergency response system that have been dispatched to their rescue. In addition, the disclosed automated triaging and dispatching can increase the number of victims assisted in the case of mass disaster scenarios. Further, the use of the dynamic network selection by the rescue application results in increased ability of disaster victims to transmit rescue requests and location updates, even during outage of one or more communication networks. As such, the embodiments described herein represent significant improvements in computer-related technology.

Various aspects of the disclosure will now be described with regard to certain examples and embodiments, which are intended to illustrate but not limit the disclosure. Although the examples and embodiments described herein will focus, for the purpose of illustration, specific calculations and algorithms, one of skill in the art will appreciate the examples are illustrate only, and are not intended to be limiting.

Overview of Example Emergency Response System Computing Environment

FIG. 1A depicts a schematic diagram of an emergency response system 100 in which various embodiments according to the present disclosure can be implemented. The emergency response system 100 includes user computing devices 110 configured with computer-executable instructions to run the disclosed rescue application 105. The emergency response system 100 further includes one or more public service answering points (PSAPs) 121 that may be integrated with one or more rescue management servers 120; the one or more rescue management servers 120 are configured with computer-executable instructions to run the disclosed rescue request manager 125. The emergency response system 100 also includes one or more responder computing devices 130 configured with computer-executable instructions to run the disclosed responder application 135.

The user computing devices 110, rescue management servers 120, and responder computing devices 130 may be in communication with one another via a network 115. The network 115 can include any appropriate network, including an intranet, the Internet, a cellular network, a local area network or any other such network or combination thereof. In the disclosed implementations, the network 115 can be dynamically selected from between the Internet and SMS based on a determination of best network subroutine. Protocols and components for communicating via the Internet or any of the other aforementioned types of communication networks are known to those skilled in the art of computer communications and thus, need not be described in more detail herein.

User computing devices 110 and responder computing devices 130 can include any network-equipped computing device, for example desktop computers, laptops, smartphones, tablets, e-readers, gaming consoles, and the like. The rescue management servers 120 can include one or more servers disposed in one or more geographic regions, for example a first set of servers that handle rescue requests within a first region (e.g., a particular zip code, city, state, or nation) and a second set of servers that handle rescue requests within a second region. Each user computing device 110, rescue management server 120, and responder computing device 130 includes hardware computer memory and/or processors, an operating system that provides executable program instructions for the general administration and operation of that server, and a computer-readable medium storing instructions that, when executed by a processor of the computing device or server, allows the computing device or server to perform its intended functions. Users can access the emergency response system 100 via their computing devices 110, over the network 115, to submit rescue request packets to the rescue management servers 120, receive dispatch arrival estimates, and/or to provide location updates to emergency responders. Emergency responders can access the emergency response system 100 via their computing devices 130 to receive dispatch assignments, victim information, and/or victim location updates.

In some embodiments, the rescue management servers 120 may transfer communications to or receive communications from an operator (for example, the PSAP agent) working in conjunction with the rescue management servers 120. For example, while the rescue management servers 120 are shown as a computing system, the rescue management servers 120 are integrated with various operators that are able to take over communications with a victim or person reporting an event via the emergency response system 100. Accordingly, the operator may interrupt operation of the rescue management servers 120 to take over a particular rescue request or may be queried or prompted for assistance in conditions where the rescue management servers 120 need assistance (for example, are unable to process communications from the user computing device 110 or similar situations).

For example, the PSAP 121 may be integrated with the rescue management servers 120 such that the rescue management servers 120 are part of the PSAP 121. As such, the PSAP 121 may receive and review communications from and/or between the computing devices 110 and the rescue management servers 120, for example via the rescue application 105 and the rescue request manager 125, among others. The PSAP 121 may be configured to handle text-to-911 message exchanges (for example, requests from victims along with communications between the PSAP and the victim via text message). For example, the computing device 110 may send SMS text messages directly to the PSAP 121 and the PSAP 121 (for example, via the rescue management servers 120) may be integrated with the text-to-911 message exchanges such that the PSAP 121 is able to receive and process said text-to-911 messages. In some embodiments, the PSAP 121 or the rescue management servers 120 may review said text-to-911 messages using an automated natural language processing application. Said text-to-911 messages may be analyzed, via machine learning, for sentiment and quantitative information that is related to a prior set of data. This analysis may be utilized in processing and/or triaging by the rescue management servers 120, for example via the rescue request manager 125. For example, the text-to-911 message may be analyzed to determine one or more factors that impact a severity analysis or determination (or any other triaging analysis, factor, or determination) for the sender.

In some embodiments, when the PSAP 121 (for example, via the rescue management servers 120) is communicating with the victim (or victim's representative) via text messaging (SMS), the PSAP 121 (for example, via the rescue management servers 120) may use decision trees, random forest, or similar processing methods or processing to request responses to particular questions. In some embodiments, the PSAP 121 (for example, via the rescue management servers 120) may include a chatbot or similar application that automatically generates PSAP text messages based on the relevant particular questions. The decision tree or other similar processing method(s) may use such questions to categorize the text-to-911 message exchange to a particular emergency medical services (EMS) or other response code (for example, via convergence or similar analysis). For example, during the text-to-911 message exchange, the PSAP (or rescue management servers) chatbot or similar application may select particular questions to ask to the victim to attempt to narrow down possible EMS or other response codes to a particular single code that best conforms to the situation based by the victim. Such questions may seek responses to questions or inquiries such as victim location, type and severity of emergency, and standard ancillary questions that define the victim's emergency/ situation with a greater degree of precision.

The PSAP 121 (for example, via the rescue management servers 120) may then measure a convergence of the text-to-911 message exchange to the triaging order based on a confidence interval or value determined from or based on a certainty of the natural language and/or other processing analysis of the text-to-911 message exchange. If the confidence interval is greater than a predetermined value (for example, 90%), then an iteration through an EMS or similar code decision tree is completed and a command is sent from the rescue request manager 125 to the responder application 135 is generated in an automated fashion based on the text-to-911 message. In such embodiments, the PSAP agent may not be involved in the text-to-911 message or may confirm one or more determinations in the code decision tree.

Alternatively, if the confidence interval does not exceed the predetermined value, one or more decisions of the decision tree may be routed to the PSAP agent (for example, via a PSAP agent application, which may be a component of the rescue request manager 125) for verification by the PSAP agent. In some embodiments, this process may involve assigning one or more PSAP agents to a particular text-to-911 message exchange, thereby allowing the one or more PSAP agents to work on a particular victim's emergency in an expedited manner.

In some embodiments, the text-to-911 message exchange may involve text messages in foreign languages, and the rescue request manager 125 and/or the rescue management servers 120 may translate received messages and translate outgoing messages, which may reduce an amount of time generally required for messaging requiring translation. Furthermore, each text-to-911 message exchange may generate various logs and a received text-to-911 message may be analyzed in view of previously text-to-911 message exchanges during the same or similar events as the previous text-to-911 message exchanges to determine appropriate responses or convergences. In some embodiments, this may be accomplished via dimensional analysis. In some embodiments, dimensional analysis comprises looking at the values of the terms and/or vector components of the equation or other mathematical object being evaluated. For example, output similarity can be determined based on identified input similarity.

There are different potential k-nearest neighbors (kNN) groupings of the current SMS request/transaction in reference to past SMS requests/transactions:

kNN over all terms of $\vec{O}$: rapidly assert a certain position of the given rescue request in the triage order. In some embodiments, this kNN process can also assert an EMS code.

kNN over components $\vec{S}$: rapidly assert an EMS code.

kNN over Substantial Question decision tree path: rapidly determine the most relevant questions to transact the remainder of the SMS request/interaction with, given past SMS interactions following an identical Substantial Question decision tree pre-path (i.e. the same sequence of questions was asked up to the point of this kNN evaluation of the current SMS transaction).

When applying the kNN dimensional analysis to the equations described herein, the values of each term in $\vec{O}$, for example, and the values of the components/dimensions of each vector in $\vec{O}$ are sequenced to compose a coordinate vector. All such vectors are composed from the current transaction or from a data lake of prior SMS rescue request transactions. All such vectors are mapped as coordinate points in an $\mathbb{R}^n$ space.

In some embodiments, a certain scenario $\vec{T}$ from the current transaction is mapped in a similar coordinate manner as above separately from each prior SMS transaction. First, the SMS transaction that is currently taking place may map an EMS code to itself, or can otherwise be dimensionally related to other prior points in the previously mentioned $\mathbb{R}^n$ space. Classifications for kNN may take place, in some embodiments, and in varying combination depending on the embodiment, for all terms $\vec{O}$, for EMS codes $\vec{S}$, for scenarios $\vec{T}$, and for decision tree paths of the kNN suggests an EMS code for the current chatbot SMS transaction based in part on the fact that similar $\vec{S}$, scenario $\vec{T}$ (i.e. both of the disaster scenarios involved floods), sentiment derived from the NLP process, etc. yielded a same EMS code or similar EMS code (with a highly similar decision tree pre-path).

In some embodiments, the rescue management servers 120, the PSAP, and/or the rescue request manager 125 may receive image and/or video files, for example via an SMS message, social media, via the rescue application 105, or other submission. In some embodiments, rescue management servers 120 and/or the rescue request manager 125 is tasked with analyzing the received image or video file to reduce a likelihood of exposing dispatchers to potentially traumatizing information or images. In some embodiments, the rescue management servers 120 and/or the rescue request manager 125 parses the image and video files and analyzes them using one or more computer vision applications and/or algorithms. In some embodiments, these applications and/or algorithms may determine location data or other information regarding severity, sentiment, situation, (for example, weapons detection) etc., from the image and/or video files.

In some embodiments, such applications and/or algorithms provides values that impact the triaging determination, specifically when a confidence interval of the detected event in the image and/or video files exceeds a specific, predetermined value. If the confidence interval does not exceed the predetermined value, the convergence of the natural language processing application is insufficient to converge on a code, a text summary of the computer vision application's classification of the image and/or video file received will be delivered to the PSAP agent for review and use in evaluating the communication.

In some embodiments, the rescue request manager 125 and/or the rescue management servers 120 collects information about events and/or victims not available through communications from victims, etc., by scraping or otherwise analyzing social media posts and communications. In some embodiments, the scraping process collects victim and/or event location severity data, and/or similar information based on detected or identified social media posts and communications. The information collected by the scraping process may be used to determine victim density during an event. Such processing may allow automatic triaging of victims that did not affirmatively generate a request via the emergency response system 100 or other PSAP communication.

The collected information may be parsed using natural language with confidence intervals or levels, similar to the discussion herein. When the confidence interval in the natural language processing of the scraped social media meets a predetermined level, the scraped social media may be used to determine an EMS or similar code. If the confidence level does not meet the confidence level PSAP agent intervention may be needed.

In some embodiments, the scraped social media may include images and/or video files that are processed via the image processing described herein. In some embodiments, the social media scraping may determine a value for victim density during an event, location data, jurisdictional boundaries, geofences, or other geographic area information, and so forth based on posts or communications collected by the social media scraping process. Such information may allow responders to be directed to areas where more people can be assisted in a given area in less time and may justify responders being able to exit jurisdictional boundaries, etc., or used in triaging. Furthermore, the social media scraping may provide for detection of victims during an event that may otherwise not requested assistance. Since some people may post on or communication via social media as opposed to using the rescue request application 105 or via phone or text-to-911 messages due to various conditions (excessive hold times, network issues, and so forth), such posts or communications may allow for said people to be identified and rescued.

Social media posts and/or communications may have a lower confidence level than direct communications. Accordingly, scraped information may be determined to be less reliable than direct communications and may be triaged at a lower level than explicit rescue requests.

Turning specifically to the roles of the different applications within the emergency response system 100, FIG. 1B depicts example interactions between the rescue application 105, rescue request manager 125, and responder application 135.

At interaction (1), the user initiates and completes the rescue request using the dynamic user interface of the rescue application 105. As described herein, the rescue application 105 can present a first user interface that allows the user to specify which type of emergency the user is experiencing. To illustrate, general types of emergencies include entrapment/crush injuries, lacerations/bleeding, burns (or heat exposure), hypothermia (or cold exposure), drowning, and assault, to name a few examples. The rescue application 105 uses the user selection made in the first user interface to determine which follow-up user interface(s) to present in order to obtain a complete packet of information relating to the emergency. These user interfaces can be selection-based (e.g., via drop down menus, selectable radio buttons and/or check boxes) in order to minimize the opportunity for errors or information omission that are associated with manual information entry. The selection-based options of the user interfaces can be designed to obtain a complete set of information, that is, all of the information needed by the emergency response system 100 in order to prioritize the rescue request and dispatch appropriate emergency responders. Optionally, the user interfaces can be supplemented with free-form text input that enables users to provide additional information. Further, rescue request can be supplemented with pre-stored medical information, or, if such information has not been pre-stored, the user interfaces can prompt the user to provide such information. This user interface provides a number of technical benefits as described herein, including minimizing the time required for the user to transmit a rescue request and ensuring that the emergency response system 100 obtains a complete set of emergency information with the initial rescue request.

The rescue application 105 may, in some implementations, receive instructions from another application regarding the information to present in the user interfaces. For example, the rescue application 105 may receive an indication from a disaster monitoring system that an earthquake has occurred in a particular area. In response to this, the rescue application 105 may include earthquake-related emergency types in the initial user interface (or surface them to the top of the initial user interface) for rescue requests placed within a region associated with the earthquake. As another example, the rescue application 105 may receive an indication that a fire is spreading, and may include fire-related emergency types in the initial user interface (or surface them to the top of the initial user interface) for rescue requests placed within a region associated with the fire, or associated with a predicted spread of the fire. This modification of the initial user interface can be performed similarly for other types of natural disasters including hurricanes, flooding, tornadoes, tidal waves, and the like, or for man-made disasters such as attacks or hazardous contamination. As such, the emergency response system 100 may include one or more computing devices implementing such disaster-monitoring applications (e.g., based on satellite imaging data, seismic sensors, weather data, social media monitoring, etc.).

At interaction (2), the rescue application 105 causes the user device 110 to transmit the rescue request to the rescue request manager 125 implemented on the rescue management servers 120. As described herein, this may involve determining a suitable network over which to transmit the rescue request.

At interaction (3), the rescue request manager 125 performs automated triaging of the rescue request with other incoming rescue requests and identifies a suitable responder to dispatch to the user. The triaging can be based, for example, on a severity of the emergency as indicated by the emergency information of the rescue request packet (e.g., criticality of any injuries, threat level of any assault), and also on a distance between the user and a nearest dispatch hub (e.g., police station, hospital, fire station). Identification of a suitable responder can include matching any injury or emergency situations with one or more of police, firefighters, emergency medical personnel, and other types of emergency responders.

At interaction (4), the rescue request manager 125 sends dispatch instructions to the responder application 135 of a computing device designated for the identified emergency responder. This can involve, for example, determining a particular ambulance that will be dispatched, identifying a computing device of the ambulance, and sending the dispatch instructions to the responder application 135 running on the computing device of the ambulance. Similar dispatch instructions can be sent to responder applications 135 of firetruck computing devices, police vehicle computing devices, and/or personal computing devices of emergency responders. The dispatch instructions can include the emergency information presented in the rescue request packet such that the dispatched emergency responder has a clear picture of the emergency at hand and can ready any required supplies and/or personnel for handling the emergency. Further, the dispatch instructions can include the location of the user computing device at the time of transmitting the rescue request and/or dispatch instructions.

At interaction (5), the responder application 135 may send a dispatch confirmation to the rescue application 105. The dispatch confirmation can alert the user that an emergency responder is on the way, and may provide information such as estimated time of arrival, route tracking, and identification of the emergency responder.

At interaction (6), the rescue application 105 can send location updates to the responder application 135. Beneficially, this can be performed in an automated fashion such that the user requesting rescue does not have to actively update the dispatched responder when his or her location changes, and so that the dispatched responder maintains an up-to-date record of the user's location. Location updates can be performed in real time, that is, as the user is moving from one location to another. Similar to transmission of the rescue request, transmission of the location updates can involve determination of a suitable communications network. Beneficially, this can continue to keep the emergency responder updated about the user's location even in the event of outage of a particular network, such as a cellular Internet network.

Interactions (5) and (6) are depicted as taking place directly between the responder application 135 and the rescue application 105. Beneficially, direct communications between these applications may reduce the amount of time required for emergency responders to obtain critical information. However, in some implementations interactions (5) and (6) may flow through an intermediary computing device, for example the rescue request manager 125.

Although not illustrated, in some embodiments one or both of the rescue application 105 and the responder application 135 can signal the rescue request manager 125 when the rescue has been completed. This signal can include information regarding whether the rescue-requesting user was successfully rescued and/or the condition of the user at the time of rescue or after treatment. The rescue request manager 125 can use this data to refine its triaging and responder-identifying algorithms in some embodiments. In some embodiments, the responder application 135 may be integrated with responder and/or hub entities, including, but not limited to, police departments, fire departments, emergency medical services, hospitals, and so forth.

Furthermore, while the description above utilizes interactions between the rescue request application 105 and the rescue request manager 125, in some embodiments, the rescue request manager 125 is able to receive details regarding rescue requests from other communications, such as SMS messages, social media scrapping, and audio/video communications. For example, the rescue request of interaction (2) may be received via an SMS message from the user's computing device 110 or via social media scraping of one or more user's social media posts. Accordingly, the rescue request manager 125 may handle rescue requests from various sources regardless of whether the rescue requests are received specifically from a rescue request application 105.

Similarly, in some embodiments, the rescue request manager 125 is able to dispatch instructions and/or receive dispatch confirmation and send/receive location updates to the responder application 135 or other communication means. For example, such exchange of information may occur via SMS message, and so forth, in situations where responders are unable to utilize or are not utilizing the responder application 135.

For example, the rescue request manager 125 receives communications from text-to-911 systems or may incorporate a text-to-911 module or system configured to handle rescue requests made over text-to-911. In current implementations, text-to-911 systems may utilize operators to obtain initial data from rescue requestors. These operators may use drop down menus or similar categorical implementations of frequently asked questions (for example, to obtain the initial data via the text-to-911 system.

Overview of Example Emergency Response System Processes

FIG. 2A is a flowchart of an example process 200 for emergency rescue requests and dispatch operations within the emergency response system 100.

The process 200 begins when a user (victim) initiates a rescue request, for example using the disclosed dynamic user interface of the rescue application 105 at block 201. From there, the process 200 branches into three routines: looking up non-emergency stored medical information at block 202, implementing a persistent location awareness subroutine at block 203, and gathering the emergency information for the emergency service request at block 204.

Once finalized, the rescue request packet is sent to the server (e.g., the rescue management server 120). From there, the process 200 branches into three routines: implementing a triaging subroutine at block 205 (for example, triage algorithm subroutine 300e described in further detail below), establishing geofences at block 206, and implementing an SMS/data parser routine at block 207.

Next, the process 200 transitions to a client security step to validate geofences at block 208, and then implements a dispatch operations subroutine at block 209 (for example, dispatch operations subroutine 300d described in further detail below).

Figure 2B:
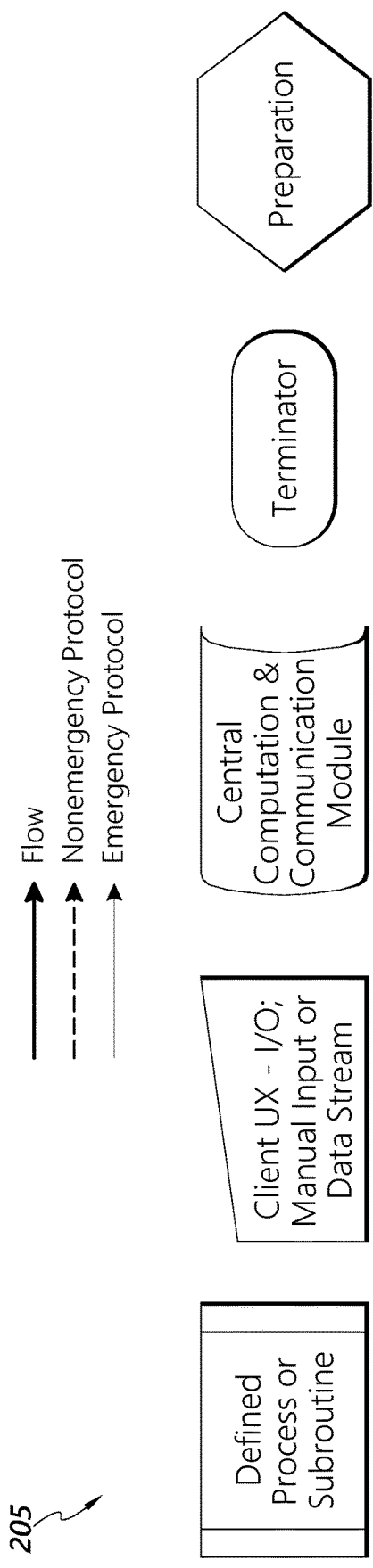
FIG. 2B is a legend relating to the flowcharts of the present disclosure.

FIG. 2B is a legend relating to the flowcharts of the present disclosure. FIG. 2B indicates that the black arrows of the flowcharts depict general data flow, while green arrows indicate a non-emergency protocol and red arrows indicate an emergency protocol. An emergency protocol refers to a protocol used during an emergency scenario such as a mass disaster or attack. A non-emergency protocol refers to a protocol used during processing of rescue requests during non-mass-disaster scenarios, for example daily rescue requests. FIG. 2B also illustrates the visual depiction of blocks corresponding to defined subroutines, client user interface input and output ("I/O") operations, central computing (e.g., by the rescue management servers 120), a termination block, and a preparation block.

Figure 2C:
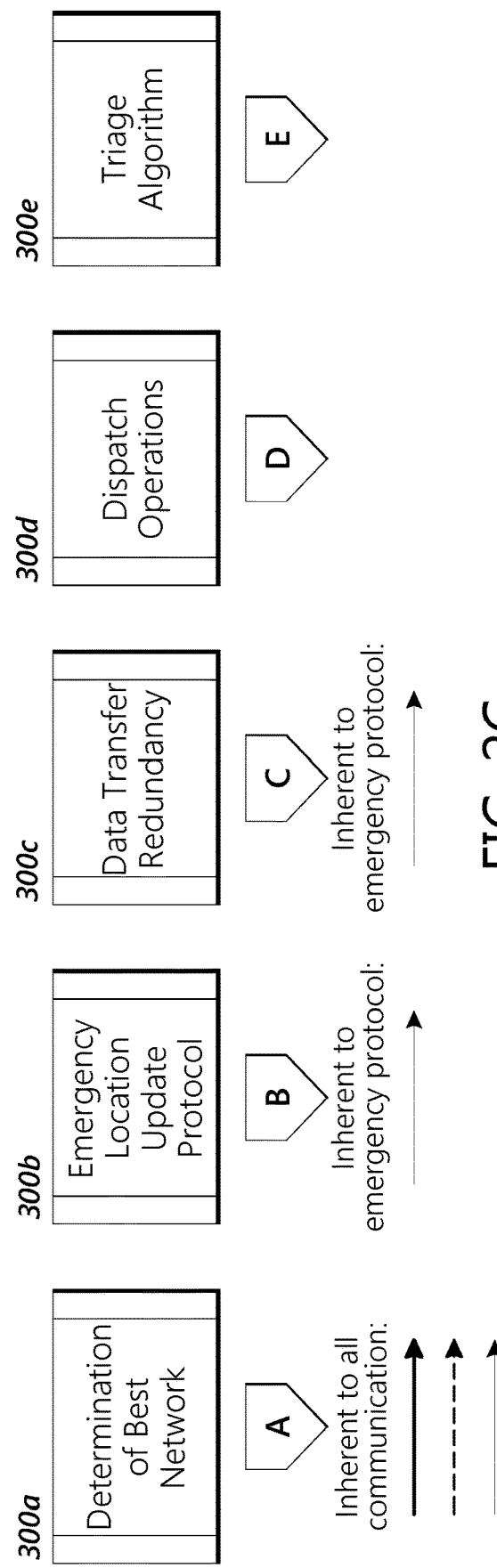
FIG. 2C depicts five subroutines of the process of FIG. 2A.

FIG. 2C depicts five subroutines that can be used in the process 200. These include subroutine A for determination of best network, subroutine B for emergency location update protocols, subroutine C for data transfer redundancy, subroutine D for dispatch operations, an subroutine E for triaging. As illustrated, subroutine A is inherent to all communications, while subroutines B and C are inherent to the emergency protocol.

FIG. 3A is a flowchart of an example process for a determination of best network subroutine of FIG. 2C. To determine the best (for example, fastest and/or most reliable) communications network, the determination of best network subroutine performs, for example, a client-side evaluation of the signal strength and volume of communications handled by a particular network (for example, cellular Internet network or the SMS text network) at block 301. The client-side evaluation may be performed at any of the user computing devices 110 (for example, via the rescue application 105), the rescue management servers 120 (for example, via the rescue request manager 125), and/or the responder computing devices 130 (for example, via the responder application 130). Based on this evaluation, the client (for example, one of rescue application 105, rescue request manager 125, and responder application 135, or the associated devices) can determine whether to use Internet or SMS (or determine the best network from among a number of other network types) at block 302. For example, if cellular Internet has failed on a certain number of user computing devices 110 running the rescue application 105, the emergency response system 100 can switch to using a lower bandwidth communications network (e.g., SMS). The emergency response system 100 can also set a requery radius to use for requerying the user computing devices 110 for any potentially missed communications. In some implementations, the determination of best network subroutine can decrement the requery rate as a function of battery life of the user computing device 110 or the responder computing device 130, for example when performed by one of the user or responder computing device 110 and 130, respectively, operating on battery power.

In some embodiments, the rescue request manager 125 tracks how many of the rescue applications 105 are able to maintain Internet versus SMS communications (or LTE vs. 2G communications, and so forth) and makes a determination to communicate with all rescue applications 105 and responder applications 135 via only the most robust network or networks. In some embodiments, the rescue request manager 125 communicates with only those rescue applications 105 and/or responder applications 135 that are unable to maintain Internet communications using SMS communications (or LTE vs. 2G communications, and so forth), and vice versa, while communicating with those rescue applications 105 and/or responder applications 135 that are able to maintain Internet communications using the Internet communications. Furthermore, the determination of best network subroutine can be made in response to concerns about network congestion, battery life of the client device, and so forth.

In some embodiments, when transmitting information (for example from the user computing devices 110 to the rescue request manager 125), an important balance exists between the quantity and quality of data to send and maintaining the battery life of the user computing device 110 of a victim. The user computing device 110 may be used to keep collecting critical information, such as location, for communication to the rescue request manager 125. Thus, it may be important to determine the best network, at block 302, over which the user computing devices 110 and the rescue request manager 125 communicate while maintaining or otherwise maximizing battery life of the user computing device 110.

In some embodiments, such a determination may be made based on various information and/or inputs from one or more of the user computing devices 110 (for example, via the rescue application 105), the rescue management servers 120 (for example, via the rescue request manager 125), and the responder computing devices 130 (for example, via the responder application 130). For example, one or more of these devices and servers may identify or measure various parameters, including, for example, network congestion, battery charge, battery consumption, signal strength, network type, and so forth, and use the identified or measured parameters to determine which communication network to use. Any of these measured parameters may be determined as part of the evaluation of block 301.

A set of equations may be used in the determination of which communication network to use following the evaluation of associated parameters. For example, the set of equations includes determinations of the network congestion or traffic ($V^*$), the strength of signal measurement ($\psi$), and/or the battery consumption (C), as shown below in Equations 1.1-1.3:

$$V^* \in \mathbb{R} : V^* = +\eta_1 V + \eta_2 \nabla V \quad \text{Equation 1.1}$$

Where:
V is representative of traffic on the network (for example, the congestion of the network);
$\nabla V$ is representative of a change to the traffic volume over a period of time. In some embodiments, the $\nabla V$ has a multivariate basis or takes the form of a stochastic partial differential equation (SPDE), as it attempted to predict cell network volume while certain events are taking place. In some embodiments, $\nabla V$ may not impact $V^*$ (for example, $\eta_2=0$) if the change in traffic volume is incalculable or irrelevant to the situations at hand, for instance during periods of normal network traffic volume;
$V^*$ is representative of a weighted sum of the current traffic volume V and a change to the volume $\nabla V$.

$$C \in \mathbb{R} : C = \frac{\partial V_p}{\partial t} : V_p \notin V \quad \text{Equation 1.2}$$

Where:
C is measured as a change in charge remaining in the battery, $V_p$ of the user computing device 110 or the responder computing device 130. A larger value for C may indicate higher consumption of charge and may merit use of an energy-inexpensive network type in order to preserve battery life.

$$\psi \in \mathbb{R} : \psi = \eta_1 F + \eta_2 \psi_s \quad \text{Equation 1.3}$$

Where:
ψ is a scalar value based on a network type F and a $\psi_s$;
F∈ℕ, is a natural number indicating a network type (for example, 2G, 3G, 4G, LTE, and so forth); and
$\psi_s \in \mathbb{R} : \psi_s > 0$, indicating a signal strength.

Based on these three equations, a value N is determined according to $N = \|<\varphi, V^*, C>\|$, where N is a real number used to determine a best network for use in communicating between devices and the server. Based on the value of N, the network for use with communications is selected based on the ranges below:

$$N < k_1 \rightarrow 2G$$

$$k_1 \leq N < k_2 \rightarrow 3G$$

$$k_2 \leq N < k_3 \rightarrow 4G$$

$$N > k_4 \rightarrow LTE$$

Where:
$k_1$, $k_2$, $k_3$, N are all real numbers.
N may be calculated based on the signal measure φ, network volume V*, and battery consumption C as constraints, where φ, V*, C hold equal influence in the generation of N.

In some embodiments, $\vec{\eta}$ is a set of weights for Equations #1.1-1.3 and where $\vec{\eta} = [\eta_1, \ldots, \eta_n]$ serves only as a set of constants. For example, in the equations above, $\eta_1, \eta_2 \in \vec{\eta}$ determine an importance of V versus VV in the calculation of V*. In some instances, $\eta_1, \eta_2$ may be determined based on previously recorded real-world scenarios and/or simulations of scenarios as they apply to the current situation. In some embodiments, determinations of $\vec{\eta}$ are separated based on whether a victim's rescue request is being processed during a disaster or during a "normal" situation. In some embodiments, $\eta_1, \eta_2$ are percentages.

In some implementations, N may utilize another transformation of the vector <φ, V*, C> before magnitude is generated. Furthermore, N may find basis in k-means or another grouping algorithm based on the direction of <φ, V*, C> on a polar graph.

FIG. 3B is a flowchart of an example process for an emergency location update protocol subroutine 300b of FIG. 2C. The emergency location update protocol begins by implementing the determination of best network subroutine 300a of FIG. 3A in order to determine which network will be used to identify and/or transmit location updates. The process can also include a subroutine at block 303 for determining t=0, which refers to the time point at which cellular internet fails, or is otherwise unusable for communication protocols. These inputs are provided to the rescue management servers 120, which then prompt user computing devices 110 and/or responder computing devices 130 to perform computations relating to determining location updates. This prompt may include information relevant to such computations, for example the length of time estimated for a responder to arrive at a given victim's location (as it would be desirable for their battery to last at least that long to continue communications with the emergency response system 100).

In some embodiments, transmission of location information utilizes power from the device battery. Accordingly, in some embodiments, the battery powered device (for example, the user computing devices 110 and/or the responder computing devices 130) may determine or decide whether to continuously transmit (for example, redundant data transfer, at block 300c, of) its location or have the device or server receiving the location information simply utilize the previously transmitted location information. In some embodiments, such a decision is based on many factors including battery life of the device, responder arrival time, the direction and velocity of a victim's travel, and the severity of a victim's emergency during the emergency response request.

In some embodiments, the determination whether to transmit the current location information is made based on a comparison of various parameters, as defined below in Equations 2.1-2.2. below:

$$T_b = \begin{cases} 0 & T < a \\ 1 & T \geq a \end{cases} \qquad \text{Equation \#2.1}$$

$$T = \left\| < \vec{l}, t_r, v_v, \frac{\partial v_v}{\partial t}, \|\vec{S}\| > \right\|$$

$$\vec{l} \in \mathbb{R} : \vec{l} = l - \nabla l \qquad \text{Equation 2.2}$$

Where:
T is a magnitude of a vector based on battery life data ($\vec{l}$), responder arrival time ($t_r$), victim device velocity ($v_v$) and acceleration $$\left(\frac{\partial v_v}{\partial t}\right)$$

and victim severity ($\vec{S}$), where $\vec{S}$ may remain in vector form but the magnitude of the vector $\vec{S}$ is extracted.

$T_b$ is a Boolean decision whose value determines whether to transmit current victim location information (for example, when $T_b$ is "0") or to use the last known victim location information (for example, when $T_b$ is "1") based on where T falls on a number range as compared to a value a.

The values of $$\left\langle \vec{l}, t_r, v_v, \frac{\partial v_v}{\partial t}, \|\vec{S}\| \right\rangle$$

may have an equal influence on the value of T and may allow for parameterization and categorization of scenarios based on different factors through vector properties (for example, direction, magnitude, and so forth), which may be useful in determining a value for a. Furthermore, each of these values may be scalar values.

A value for a is chosen based on a moving average (or similar calculated value) of past values of T based on an optimal choice $T_b$ (of whether to transmit new data or use last known data) in real or simulated victim scenarios.

$\vec{l}$ is the battery life data for the device and is based on the difference between current battery power remaining (l) and the consumption rate of battery power ($\nabla l$).

$t_r$ is the responder arrival time, which may comprise an amount of time before the responder arrives at a location of the victim. In some embodiments, the responder arrival time is pinged from the server 120 and/or predicted client-side, depending on battery life, determination of the best network, and so forth.

$v_v$ and $$\frac{\partial v_v}{\partial t}$$

represent velocity and acceleration of the device in question. These values are computed from device onboard accelerometers and/or other sensors.

$\|\vec{S}\|$ represents the victim severity. $\|\vec{S}\| \equiv S$ or $\vec{S}$ (whichever input is most effective and/or more logically appropriate).

Figure 3C:
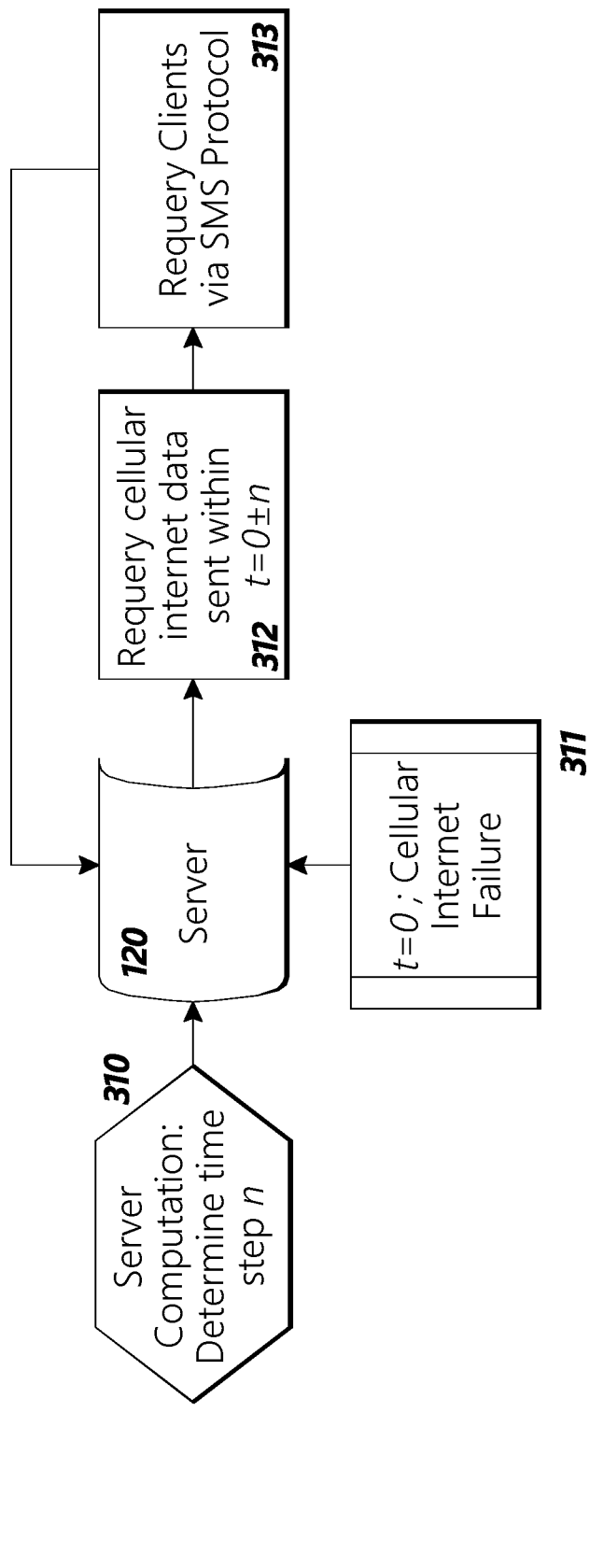
FIG. 3C is a flowchart of an example process for a data transfer redundancy subroutine of FIG. 2C.

Next, the process can implement the data transfer redundancy subroutine 300c described in more detail with respect to FIG. 3C. The process can switch to SMS updates at block 305, for example, for increased reliability during disaster situations.

The process 300b can also implement a client-side opportunity cost analysis at block 306 to determine whether to preserve battery or send location update data. The criteria used in this analysis can include the rate of power consumption by the device, remaining battery reserves, and an estimated time until rescue. If it is decided to preserve battery, the process can use the last known location (e.g., at t=0) at block 309 to identify a predicted location. Alternatively, the process 300b can extrapolate the predicted location from the last known location and information including velocity and trajectory of the computing device prior to network failure.

If it is decided to send location update data, the process 300b can determine the ability to provide GPS data at block 307 and then determine whether to update GPS via SMS at block 308. If so, the process 300b loops back to the server computations. If not, the process 300b again can use the last known location or predicted current location (e.g., at t=0).

As will be appreciated, for privacy reasons the location information may be controlled by a third party (e.g., the rescue management servers 120) and selectively disclosed as needed via designated protocols. For example, victim location data may only be disclosed to the particular emergency responder dispatched to the victim.

FIG. 3C is a flowchart of an example process for the data transfer redundancy subroutine 300c of FIG. 2C. The data transfer redundancy subroutine 300c can be implemented by the rescue management servers 120 in some implementations. To begin, the process 300c performs preparation computations to determine time step n at block 310. Time step n refers to a range of time computed by the server for which data sent via cellular internet during this interval will be required. The process 300c can also include a subroutine 311 for determining t=0, which refers to the time point at which cellular internet initially failed, or was otherwise unusable for communication protocols. In some embodiments, the subroutine 311 may include one or more blocks of the subroutine 300b or may comprise the subroutine 300b. These inputs are used for server computations relating to data transfer redundancy.

Next, the server 120 requires cellular internet data sent within a time frame between t=0 and t=n at block 312. This range represents the range of timestamps for which the server 120 will requery communications across the emergency network. Accordingly, the server 120 will seek to request that communications that occurred during the range 0<t<n be rebroadcast to prevent data loss. This requery can be performed via an SMS protocol, via block 313, in the event of cellular Internet failure or via any other communication protocol, dependent on the current or expected communication conditions.

In some embodiments, if the communication networks fail and transfer of information between devices and the server is terminated, information useful in the rescue of victims could be lost. In order to ensure that sufficient information is available to the rescue request manager 125 to triage victims and provide data to the responder applications 135, a time window for which information will be re-queried over an appropriate communication network 115 is determined by one or more of the rescue applications 105, rescue request manager 125, and the responder applications 135.

Equation 3.1 below provides for determining the time step n at which data transfer re-querying is performed.

$$n = \eta_1 * d_{std} + \eta_2 * d_{act} + \eta_3 * d_{sim} \qquad \text{Equation 3.1}$$

Where:

$d_{std}$ represents a standard or expected downtime. $d_{std}$ may be determined as a moving average of the standard downtime in a specific scenario; in some embodiments, $d_{std}$ is determined using other mathematical correlations. For example, during a flood scenario, the standard downtime, $d_{std}$, for a particular communications network may be 4-hours while an urban terrorist attack has a standard downtime, $d_{std}$, of approximately 5-minutes.

$d_{act}$ represents how long the downtime has been at the current time (for example, at the time that the current calculation is being performed), as measured by the rescue request application, the rescue request manager, or the responder application.

$d_{sim}$ represents a simulated downtime for the specific scenario as obtained from various computations/models of downtime.

$\eta_1, \eta_2, \eta_3$ are percentages representing weights applied to the $d_{std}$, $d_{act}$, and $d_{sim}$ variables, where the percentages sum to equal 1.

In different scenarios or events, the weights applied to the different downtimes may change. For example, in more common events, the standard or expected downtime may be more highly weighted as compared to less common events because, for the more common events, more previous downtimes are available to determine the standard or expected downtime, thereby making the standard or expected downtime in more common events. Thus, in more common events, the standard downtime $d_{std}$ may have a higher value weight $\eta_1$ than in the less common events. Similarly, the actual downtime and the simulated downtimes may have varying weights dependent on the scenario and the trust or confidence in the respective downtime values.

For example, in a first scenario, the $d_{std}$, $d_{act}$, and $d_{sim}$ have weights of 0.1, 0.1, and 0.8, respectively. Accordingly, in the first scenario, the simulated downtime is weighted the highest, indicating that the simulated downtime is strongly applicable to the scenario and that the models provide the expected downtime with the highest confidence level, as compared to the standard downtime and the actual downtime. In a second scenario, $d_{std}$, $d_{act}$, and $d_{sim}$ have weights of 0.3, 0.6, and 0.1, respectively. This indicates that the actual downtime already experienced has the highest confidence level, with low confidence in the simulated downtime and middling confidence in the standard downtime, suggesting that the emergency response system 100 may be unfamiliar with the current scenario or may have insufficient data to properly predict downtimes based on simulations or previous scenarios.

Figure 3D:
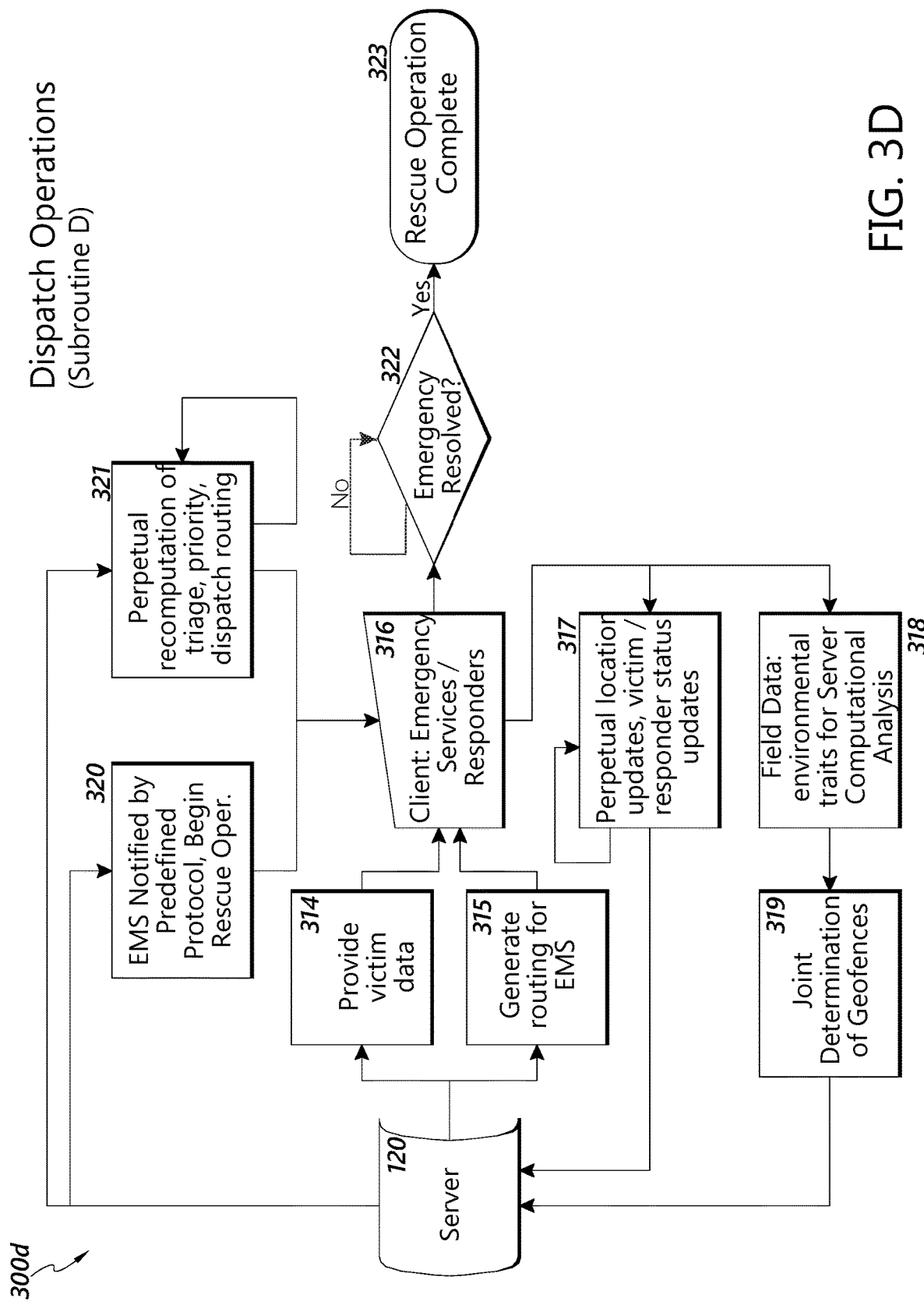
FIG. 3D is a flowchart of an example process for a dispatch operations subroutine of FIG. 2C.

FIG. 3D is a flowchart of an example process 300d for the dispatch operations subroutine of FIG. 2C. The dispatch operations subroutine can be implemented by the rescue management servers 120 in some implementations. The dispatch operations process 300d can include provision of victim data (e.g., from the rescue request packet) at block 314 and routing information from the rescue request manager 125 at block 315 to a responder application 135 (represented in FIG. 3D by the client: emergency services/responders block) at block 316. The responder application 135 can receive perpetual (e.g., real-time) location updates and/or status updates relating to the victim, and can also provide perpetual location and/or status updates relating to the emergency responder at block 317. The responder application 135 can also use field data for determination of geofences at block 318, jointly with the rescue management servers 120 in some embodiments at block 319. These geofences can be used by the rescue management servers 120 to identify emergency responders for particular rescue requests.

The rescue management servers 120 can notify the emergency responder by a predefined protocol to begin a rescue operation at block 320. The rescue management servers 120 can also perform continuous or intermittent recomputation of triage, priority, and dispatch routing at block 321.

When the responder application 135 indicates that the emergency is resolved at block 322, the rescue operation can be considered complete at block 323.

In some embodiments, the natural disaster or emergency impacts paths or routes available to emergency responders. Alternatively, or additionally, prior art systems and applications may fail to account for changing environmental factors within geofences of a particular responder. For example, the prior art systems may be unable to adapt route planning and/or assignment based on changes in the impacted environment due to the emergency, such as how a fire or flood may expand or grow in affected area and cause particular routes to become impassible as time passes. In some embodiments, as the available paths or routes change, the distance that the response must travel to reach a destination at which a victim is to be rescued may change, increasing or decreasing as time passes. In some embodiment, the distance to be traveled by the responder may be a factor that impacts the calculation of the triage order (Equation 5.1 or Equation 6) below. Furthermore, another factor that may impact the calculation of the triage order in Equation 5.1 or Equation 6 is whether responders are allowed to exit any existing jurisdictional boundaries, which may greatly impact the calculation of the triage order. Accordingly, in some embodiments, travel impedance (and dynamically changing travel impedance) and/or geofencing factors are used to determine a routing coefficient, which may be determined using the rescue request manager 125.

The routing coefficient, r, may represent the shortest and/or safest distance over which the responder travels to perform a rescue. The routing coefficient may be generated based on a path, represented by L, that the responder may take to rescue the victim. For example, for the responder to reach and rescue the victim, the responder may travel any of a number of paths or routes L from a starting location of the responder to the location of the victim. Each of the paths or routes L may have a corresponding routing coefficient, r, by which each the paths or routes L may be compared to each other to enable selection of the path or route L that is the shortest and/or safest distance for travel by the responder. In some embodiments, the preferred path or route L is the path or route L with the smallest, or minimum, r.

In some embodiments, the routing coefficient r is determined based on the path or route L for traversing a particular distance. The path or route L may be determined based on a time-parametrized scalar field bitmap, $B(\tau)$, or a matrix of values. When determined based on the scalar field bitmap, $B(\tau)$, the $B(\tau)$ may be represented by a plurality of segments or cells that each have a corresponding impedance value, $\upsilon$, that changes over time. The total routing coefficient r may be the combination of the impedance values, $\upsilon$, for each of the segments or cells that make up the bitmap, $B(\tau)$, of the path or route L. The routing coefficient r for the path or route L may be determined based on Equation 4.1 below:

$$r_n = \int_{L_n} B(\tau) ds \Sigma_{i \in L_n} \upsilon_i \qquad \text{Equation 4.1}$$

Where, r is the routing coefficient for the path or route L and is the sum of the impedance values for the path or route L. The determination of the routing coefficient r is based on a predefined time step $\Delta \tau$ between each victim and/or hub for each potential path or route L over the whole bitmap. As noted above, the lowest or minimum value routing coefficient r may indicate the most efficient or optimal route or path L.

In some embodiments, the bitmap, B, may represent a numerical array or matrix. B may be generated from location imagery. Data overlays and, in some embodiments, computer vision applications may assign impedance values $\upsilon$ to each cell or portion of the bitmap. For example, roads that are paved and generally have low traffic congestion may have a low (or negative) impedance value because they facilitate travel while roads that are not paved or generally have high traffic congestion may have a high (or positive) impedance value because they impede travel. Cells or portions of the bitmap, B, may exist within a disaster area, A. The disaster area, A, may be bounded by cells or a boundary defined by $\partial A$. Cells within the disaster area, A, and inside the boundary, $\partial A$, may have a high impedance because roads and paths within the disaster areas are generally difficult and dangerous for responders to travel. On the other hand, cells that are not part of the disaster area, A, outside the disaster area, A, may be easier to travel and, thus, have a lower impedance. In some embodiments, route planning outside of the disaster area, A, may account for changes in the disaster area, A. For example, models predict the spread of a disaster area over time and generate an injective data overlay onto the cells of the bitmap, B. This overlay may predict changes in the area, A, and/or the warping of $\partial A$, and resulting changes in v. Accordingly, responder routes may be configured to account for changing environments.

To reduce computing expenses regarding calculating the routing coefficient, r, only those routing coefficients for paths, L, that satisfy a threshold level of efficiency are calculated. Accordingly, the routing coefficient, r, for those paths, L, which would be exceedingly inefficient in terms of path length are not calculated. For example, the path, L, may be constrained by the Djikstra algorithm, or another network analysis algorithm. In some embodiments, the routing coefficient, r, for various paths, L, can be calculated using semi-stable gradient analysis (for example, path avoidance of defined area impacted by the disaster or event that is greater than a boundary of the defined area impacted by the disaster or event) where the routing coefficient values are unreasonably high, for example implying that the defined area is dangerous to travel through to takes an excessive amount of time to travel through. In some embodiments, such analysis may be carried out using machine learning algorithms. In some embodiments, the bitmap B may be represented as a vector field or as a matrix. This may allow for more complex analyses of responder speed, other impedance factors that impact responder travel through the defined area, and so forth.

The routing coefficient, r, may be computed according to Equations 4.2-4.3 below:

$$\upsilon_i = [\eta_a \cdot (\xi_a + A) + \ldots \eta_b (\xi_b + B)] \qquad \text{Equation 4.2}$$

$$r = \min([r]) = \min(\{r_1, \ldots, r_n\}) \qquad \text{Equation 4.3}$$

In Equation 4.1, r is the routing coefficient for the path or route L and is equivalent to a sum of the impedance values for all of the traveled cells of the path or route L. In equation 4.2, $\upsilon$ represents the impedance value of traveling along at least a portion (for example, a cell) of the route L such that a sum of the impedance values for the entire route L provides the routing coefficient for the route L. The lowest routing coefficient r for all possible routes L may be selected. In Equation 4.2, each v impedance value may be determined by a set of impact factors and noise terms thereupon (to reflect the degree of randomness/variability to which such terms may be subject, and hence assist in the prediction of change to these values).

In the Equations 4.1-4.3, $\eta_1, \ldots, \eta_{1n}$ is a set of weights that are applied to factors comprising impedance values of cells in the bitmap B. These weights may be determined by machine learning simulations ascribing the importance of each (positive or negative) impedance factor to the given cell in the bitmap B. In some implementations, the basis for the determination of weights via machine learning is based on past overlay data, and past real-world, or simulated scenarios. More generally, the weights $\eta$ are determined via a similar process.

In some embodiments, the routing coefficient of a particular route L may impact how that particular route or rescue is triaged as compared to other routes L. For example, Equation 5.1 below provides for an ordering of rescue requests based on weighted routing coefficients and weighted severity vectors or severity vector magnitudes.

$$\vec{o} = \eta_1 \cdot \|\vec{s}\| + \eta_2 \cdot r \qquad \text{Equation 5.1}$$

According to Equation 5.1, rescues of victims may be carried out over a path having the routing coefficient of r such that for identical values of the first term, rescue requests with lower routing coefficients are completed first, as victims making such requests may be saved faster, in a more safe manner for responders, or over a shorter distance.

In some implementations, an additional factor is included into the order equation of Equation 5.1, as will be described in further detail below.

Further to Equation 4.2 above, Equation 5.2 below may represent one of the further equations used to determine the impedance of travel of the responder to the victim for rescue:

$$\upsilon_i = [\eta_1 \cdot (A + \xi_A) + \eta_2 \cdot (\partial A + \xi_{\partial A}) + \eta_3 \cdot (C + \xi_C) - \eta_4 \cdot (R) - \eta_5 (m)] \qquad \text{Equation 5.2}$$

In Equation 5.2, the impedance of traveling along at least a portion of a route is shown as a function of four weighted values or factors. The weight values include $n_1$, $n_2$, $n_3$, $n_4$ and are applied to the factors $(A+\xi_A)$, $(\partial A+\xi_{\partial A})$, $(C+\xi_C)$, $(R)$, and $(m)$. In the above example, A is a current area in which the event or disaster occurs for a given cell of the route L and $\partial A$ is a current boundary of the area, or representative of the possible expansion of the disaster boundary. The term C may be associated with a magnitude of traffic congestion along the route L (for example, in some embodiments, a combination of an average vehicle speed and vehicle density for a given stretch of road). The term R may be associated with a working road (in some embodiments, a type of road with greater throughput potential may have a greater magnitude of negative impedance). The term m may represent a distance (for example, in one of miles, kilometers, and so forth) by which the responder may exit its jurisdictional geofence in order to carry out a respective rescue. Generally, it would be disadvantageous for the responder to exit its jurisdictional geofence, unless the victim they would be attending to is experiencing a particularly severe calamity making it unreasonable to limit rescue to only responders within the corresponding geofence.

Figures 1, 3E:
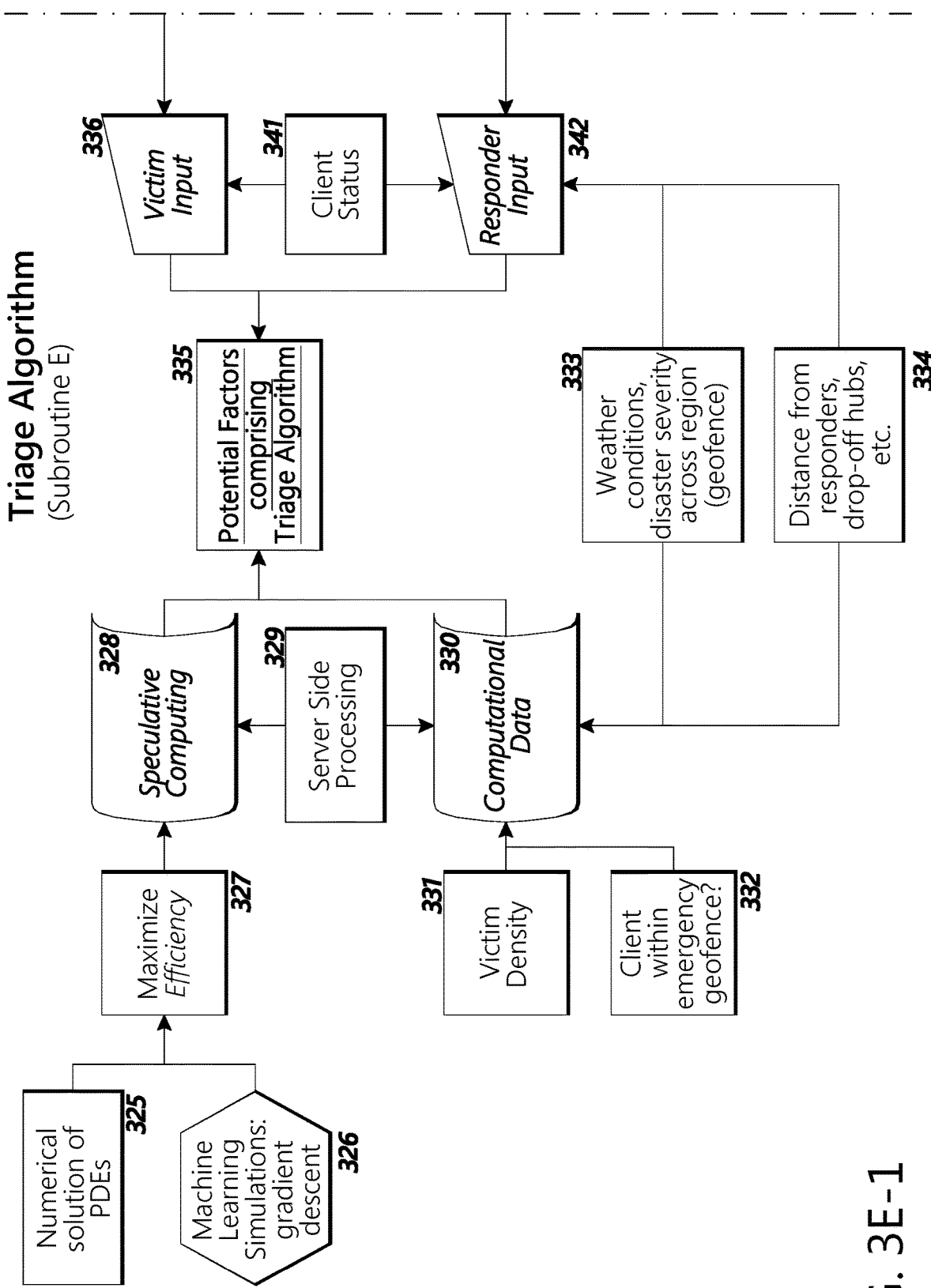

FIG. 3E is a flowchart of an example process 300e for the triaging subroutine of FIG. 2C. The triaging subroutine processes a variety of inputs to sort and prioritize incoming rescue requests and match victims with suitable responders at block 335. The branches of the process leading into the victim input block 336 represent the various inputs made by users into the rescue application 105 user interface at blocks 338-340. A relative priority value can be computed based on these inputs at block 337 and analyzed as a victim input by the triaging algorithm at the block 336. The triaging algorithm also receives a responder input at block 342 representing the availability and capacity of responder transports at block 343.

The triaging subroutine also accounts for factors such as victim density at block 331, whether a particular rescue request originates within a region of a known hazard or disaster (an "emergency geofence") at block 332, weather conditions and/or disaster severity at block 333, and distance of victims from responders and drop off hubs at block 334. Victim density at block 331 refers to the number of rescue requests originating from a particular region. For example, yield of rescues may be improved by sending responders to areas with high victim density. Other factors that can be input into the triaging subroutine include the velocity of the user device submitting a rescue request, other actions being taken on the device submitting the user request (e.g., messages or social media posts corroborating, contradicting, or providing further information about a rescue request), and touch patterns of the user while submitting the rescue request.

As shown in FIG. 3E, the triaging subroutine can involve numerical solutions of partial differential equations (PDEs) at block 325. This refers to the computation of responder pathways. This computation can take into account jurisdictional boundaries ("responder geofences") representing the geographical limits of an area to which a particular emergency responder may travel. In some implementations, the responder pathway computation can analyze rescue requests at or near such boundaries and compute whether it would be more efficient if a particular responder was able to operate outside of their jurisdiction to answer the rescue request. The responder pathway computation can be performed, for example, based on routing equations developed by the machine learning simulations.

The machine learning simulations at block 326 trains the triaging subroutine to generate pathways in various emergency scenarios. The machine learning simulations can run intermittently or periodically, for example while the rescue management servers 120 are idle or have a threshold amount of computing bandwidth. In other implementations the machine learning simulations can run on dedicated hardware. The machine learning simulations represent a training of the system to optimize responder pathways. The simulator can generate "random" situations: rescue requests relating to different types of emergencies, of different severities, in different locations, alone or in combination with other emergencies. For example, the machine learning simulations can train the system how to most efficiently dispatch emergency responders to victims requesting rescue during different disaster scenarios such as fires, hurricanes, and earthquakes.

The computed responder pathways and machine learning simulations can be constrained to maximize efficiency at block 327, that is, to maximize the number of victims rescued within a certain period of time. The responder pathways, weather conditions, disaster severity, locations of responders and drop-off hubs, victim density, and locations of any emergency geofences are provided to the speculative computing module. The speculative computing module at block 328 continues testing new pathways even as dispatched responders are en route, in order to compensate for changing conditions, changing volume and distribution of rescue requests, and completed rescues. The results of the speculative computing module are also provided to the triaging algorithm at block 335.

Equation Set 1:

As a simple example, the triage algorithm can determine triage order using the following Equation 6, where incoming rescue requests are sorted by O:

$$O = S * d \qquad \text{Equation 6}$$

where O represents a sort order score, S represents severity of the emergency information in the rescue request, and d is the distance between the user device location and the nearest responder hub. Thus, the sort order score, O, of a particular victim may be based on a severity, S, of the emergency information in the rescue request received from or about the particular victim and a distance, d, between the nearest hub and the user device location.

The victim with the highest O value can be matched first with an emergency responder. The relative severity S is subject to various input specificities, and environmental factors. For example, a severity score can be generated from the responses to UI prompts, based on EMS Priority Dispatch Codes, and based on other factors such as analysis of the user's behavior on their computing device during, before, and/or after submission of a rescue request (e.g., communications with others about the emergency, other applications in use on the mobile device, touch patterns on the mobile device). The distance d can be computed by the Haversine formula, over the curved surface of the Earth.

In this simple example, the sort order score O can be considered as a two dimensional vector, with one dimension corresponding to severity and the other dimension corresponding to distance. However, the sort order score O can be extended to any n-dimensional vector, where the overall magnitude of O would be considered as the sort order score. Each of the n-dimensions can be a different factor affecting successful rescue of a victim, as described above with respect to the triaging subroutine. These factors may be scaled so that a single step in a direction for one dimension would be equal to a single step in a direction for the other dimensions.

In some implementations, the severity score, S, or a certain input in the rescue application 105 user interface can be associated with a time limit representing a limited window for successful rescue of the victim. These time limits may be associated with particular EMS codes and/or learned from analyzing historical emergency rescue requests and their associated outcomes. As such, one factor for computing O may be such a time limit. Additionally or alternatively, O may have a time limit attached to it.

In some embodiments, when many victims request assistance at one time, for example via the rescue application 105, the rescue request manager 125 may generate an order or priority according to which each victim is scheduled to be picked up. This allows for triaging of the victims, after which responders are dispatched according to the order or priority via communications from the rescue request manager 125 to the responder application 135. In order to prioritize victims and establish the rescue order, one or more equations may be applied to generate an order output based on factors that influence the relative urgency of a victim's need to be rescued.

Equations 6 below may be solved to generate the order or priority of victim rescue. Equation 6 generates the order output and accounts for various factors. These factors may be indicated as $f$ as described herein. Accordingly, in Equation 7 below, O is the order of victim rescue as generated by the rescue request manager 125 and $f$ refers to one or more factors that operate as inputs to the order equation(s).

$$O: \mathbb{R}^n \to \mathbb{R}$$

$$\vec{O} = \|\vec{f}\| = \|<f_1, \ldots, f_n>\|$$

$$\text{Let } [f_1, \ldots, f_n] \subseteq \vec{f} : \mathbb{R}^n \to \mathbb{R} \qquad \text{Equation 7}$$

Some examples of these functions $f$ include code determination (for example, one or more of severity code, EMS code, and police department (PD) code). Additional examples of such functions $f$ include: medical ID/pre-existing condition functions, client input functions (for example, to determine whether the client provided an input or, if they have not, whether they are located within a disaster region), distance functions (for example, to determine a distance between the client and at least one responder), responder hub locations functions, weather data overlay functions, jurisdictional geofence functions, victim density functions, disaster trajectory models, social media scraping (for example, to determine nature of disaster or locations of victims), UX behavior analysis functions (for example, swipes, interaction speed), and so forth.

In some embodiments, each of the functions will have an equal impact or influence on the generated order of victim rescue. Alternatively, one or more of the functions will be more highly influential on the generated order than other functions. Accordingly, the functions allow for parameterization and categorization of scenarios based on different factors through vector properties, such as direction, magnitude, and so forth.

For example, a magnitude of a vector, whose basis is constructed from vectors of equal weight, allows for the differentiation of scenarios with similar severity (or other) scores but different basis values. In some embodiments, the parameterization and categorization of scenarios based on different factors through vector properties allows for such differentiation. Furthermore, such vector differentiation may allow distinctions regarding the most appropriate type of response to command to deploy to rescue a particular victim or victims. For example, different combinations of values of components (for example, functions) of O are grouped into different response types via k means or a similar algorithm by the rescue request manager 125 as a pre-request step. This may allow for particular distinctions to be made. For example, a "life over property" distinction may be beneficially made. For example, if a first order equation represents a rescue request regarding an assault, such a request may warrant one or both of a medical and police response. However, a second order equation may represent a non-emergency break-and-enter that may warrant a delayed and less aggressive police response and potentially no medical response. Thus, where order equations have unequal inputs, different response types may be warranted.

In some embodiments, the use of order equations may allow a large number of victims to be helped in an appropriate order that maximizes rescues (of victims) as a function of time. The rescue request manager 125 may implement the triaging subroutine to create the order, O, by which victims of the disaster or event will be rescued. The triaging subroutine may accomplish this or otherwise generate the order equations, O, by sorting priority of victims requesting rescue or assistance and assigning them to corresponding responders using the responder application 135. In some embodiments, the triaging subroutine may implement one or more equations that factor in victim, situational, and environmental data to triage the victims, where the data used is one or more of known data, estimated data based on prior disasters, and predictions of future conditions and/or based on simulations.

In some embodiments, these order equations, which may incorporate stochastic noise terms $\xi$, generate the most efficient order for rescuing victims upon solving. In some embodiments, the order equations may include both deterministic components and stochastic components. These equations may be solved directly or numerically; in some embodiments, these equations may be solved using a mesh-independent system to reduce computation costs. In some embodiments, the ordering equations may utilize a severity plane, $M_\mathbb{R}$, which provides for plane mapping and smoothing of all possible situational configurations of severity, S. Severity may relate to how severe a particular victim's rescue request is (for example, how severe the specific situation is for that particular victim). In some embodiments, the severity plane $M_\mathbb{R}$ is based in Euclidian Hilbert space and may be generated from a discrete set of known scenarios, $M_d$, as described further herein.

A first example of the order equation introduced above that further takes victim severity, smoothed victim severity, rate of change of victim lifespan with respect to time, and victim's distance from nearest responder or responder hub into account is introduced below as Equation 8.1.

$$\vec{O} = \eta_1 \vec{S} + \eta_2 \nabla^2 M_\mathbb{R}(\vec{S}) + \eta_3 \frac{\partial T}{\partial t} + \eta_4 d \qquad \text{Equation 8.1}$$

In Equation 8.1, $\vec{S}$ represents the victim's severity vector, having a magnitude and a direction. Alternatively, the severity score $\|\vec{S}\|$ can be used and d represents the distance (for example, in kilometers) for a victim from the nearest responder or responder hub. Furthermore, $\eta_1, \eta_2, \ldots, \eta_n \in \vec{\eta}$ is a set of weights applied to terms of the order Equation 7.1 above and 7.2 below. These terms ascribe a certain importance to each term of the respective order equation. The methodology of their determination is elaborated herein.

Furthermore, $$\frac{\partial T}{\partial t}$$

represents the rate of change with respect to time of a victim's lifespan, T, before rescue of the victim. In some embodiments, different EMS/PD codes assigned to a particular user rescue request may assign a victim a certain lifespan within which the victim is to be rescued. For example, broken limbs may have a lifespan of T=4 hours while a cardiac arrest episode may have a lifespan of T=5 min. An assigned value for T may be based on the victim's initial severity score (for example, when the victim initially requests rescue). In some embodiments, changes in the rate of increase or decrease of a victim's lifespan value, driven by updated victim data, can have critical importance on that victim's rescue.

Alternatively, a more complex extension of Equation 8.1 provides an order equation that takes into account victim severity, mapped and smoothed victim severity (for example, discrete plane Laplacian of victim severity), approximated plane Laplacian of victim severity, rate of change of victim lifespan with respect to time, victim's distance from nearest responder or responder hub, a routing coefficient, environmental impedance, and rate of change of environmental impedance with respect to time.

A second example of a solely deterministic equation involving stochastic components through formation into $\vec{O}$ is shown in Equation 8.2 below:

$$\vec{O} = \eta_1 \vec{S} + \eta_2 \nabla^2 M_d(\vec{S}) + \eta_3 \nabla^2 M_\mathbb{R}(\vec{S}) + \qquad \text{Equation 8.2}$$
$$\eta_4 \frac{\partial T}{\partial t} + \eta_5 d + \eta_6 r + \eta_7 W + \eta_8 \frac{\partial W}{\partial t}$$

Newly introduced values in Equation 8.2 include the routing coefficient, r, which is a method of triaging based on the path a responder would take to rescue a victim, as described herein. Some examples of additional deterministic factors with additive and/or multiplicative noise terms are now described:

W may represent a unit of conditional impedance. This impedance may embody an impact of environmental conditions on the severity of the victim's condition after the initial evaluation of $\vec{S}$. For example, the trajectory of a flood or forest fire disaster crossing over the location of a victim would increase the conditional impedance and, accordingly, the priority of that victim's rescue so as to ensure the victim is rescued before the disaster reaches them. Further, $$\frac{\partial T}{\partial t}$$

represents the change in the conditional impedance over time (for example, worsening conditions as they apply to a victim may raise a victim's order score). Thus, in some embodiments, the environmental conditions may impact the victim's change in conditional impedance, for example if the environmental conditions will threaten the victim (for example, a flood or fire may change the victim's conditional impedance if it increases risk of injury to the victim).

Newly introduced values in Equation 8.2 include the routing coefficient, r, which is a method of triaging based on the path a responder would take to rescue a victim, as described herein. Some examples of additional deterministic factors with additive and/or multiplicative noise terms are now described:

The following Equations 8.3 and 8.4 are generated as concrete stochastic order equations while adhering to the deterministic Equations 7.1 and 7.2 above:

$$\vec{O} = \eta_1 \vec{S} + \eta_2 \nabla^2 M_{\mathbb{R}}(\vec{S}) + \eta_3\left(\xi_\alpha \frac{\partial T}{\partial t} + \xi_\beta\right) + \eta_4(d + \xi_b) \quad \text{Equation 8.3}$$

$$\vec{O} = \eta_1 \vec{S} + \eta_2 \nabla^2 M_d(\vec{S}) + \eta_3 \nabla^2 M_{\mathbb{R}}(\vec{S}) + \eta_4\left(\xi_\alpha \frac{\partial T}{\partial t} + \xi_\beta\right) + \quad \text{Equation 8.4}$$
$$\eta_5(d + \xi_b) + \eta_6(r + \xi_\alpha) + \eta_7 W + \eta_8\left(\frac{\partial W}{\partial t} + \xi_\beta\right)$$

Newly introduced values in Equation 8.2 include the routing coefficient, r, which is a method of triaging based on the path a responder would take to rescue a victim, as described herein. Some examples of additional deterministic factors with additive and/or multiplicative noise terms are now described:

$$\eta_a W + \eta_b\left(\frac{\partial W}{\partial t} + \xi_\beta\right):$$

This factor represents the environmental impedance, and the rate of change with respect to time thereof. An additive noise term is included with the partial derivative with respect to time of W to quantity variance in the change of environmental conditions.

$\eta_b(d+\xi_b)$: This factor represents the distance d of the victim from the nearest responder or responder hub, depending on the implementation. An additive noise term is included to quantify standard variance in distance which may impact triage calculations.

$$\eta_\phi\left(\xi_\alpha \frac{\partial T}{\partial t} + \xi_\beta\right):$$

This factor represents the rate of change with respect to time of a victim's lifespan before rescue. An additive noise term is included as well as a separate multiplicative noise term. The lifespan of a victim before rescue that changes over time is subject not only to an addition of noise based on environmental factors, but the basis of the rate itself is subject to multiplicative environmental volatility as survivability is much less predictable as related to any given change of circumstances.

$\eta_\alpha(r+\xi_a)$: This factor represents the routing coefficient r calculated in Sub. D. FIG. 3D. The additive noise term is included to quantify standard variance in distance. In some implementations, the variability in r may be supplemented or countered by the additive noise term.

Based on the Equations 8.3 and 8.4 above, additional equations, for example a template of SPDEs Equations 8.5-8.7 below, may be generated to allow for and/or otherwise determine different factors for triaging victims in various combinations.

$$\vec{O} = \vec{O}_d + \vec{O}_s \quad \text{Equation 8.5}$$

$$\vec{O}_d = (\eta_i \cdot k_i + \ldots + \eta_j \cdot k_j) + \quad \text{Equation 8.6}$$
$$\left(\eta_a \cdot [\nabla^2 M_a(\vec{S})] + \ldots + \eta_b \cdot [\nabla^2 M_b(\vec{S})]\right) +$$
$$\left(\eta_n \cdot \frac{\partial N}{\partial t} + \ldots + \eta_m \cdot \frac{\partial M}{\partial t}\right)$$

$$\vec{O}_s = (\eta_a \cdot [A + \xi_a] + \ldots + \eta_b \cdot [B + \xi_b]) + \quad \text{Equation 8.7}$$
$$\left(\eta_a \cdot \left[\frac{\partial A}{\partial t} + \xi_a\right] + \ldots + \eta_\beta \cdot \left[\frac{\partial B}{\partial t} + \xi_\beta\right]\right) +$$
$$\left(\eta_{\phi 1} \cdot \left[\xi_{\lambda 1} \cdot \frac{\partial P_1}{\partial t} + \xi_{\lambda 2}\right] + \ldots + \eta_{\phi 2} \cdot \left[\xi_{\lambda 3} \cdot \frac{\partial P_2}{\partial t} + \xi_{\lambda 4}\right]\right)$$

For the Equations 8.5-8.7, each type of term and the beneficial purpose of its inclusion in the system is described below:

$(\eta_i \cdot k_i + \ldots + \eta_j \cdot k_j)$: This set of terms encompasses scalar values, or simple number values. This term type is beneficially included in the system of equations, because it allows simple values such as, in some embodiments, a refined severity score, distance from responders, distance from nearest responder hub, routing coefficients, vector magnitudes, and other relevant number values to be taken into account.

$(\eta_a \cdot [\nabla^2 M_a(\vec{S})] + \ldots + \eta_b \cdot [\nabla^2 M_b(\vec{S})])$: This set of terms encompasses the value of the Laplacian of a plane mapping $M_n$ with a basis of severity coordinates, whereas $\vec{S}$ is a point on such a plane comprising a given victim's severity score or vector, and is the point of evaluation for which the Laplacian is generated. This term type is beneficially included in the system of equations, because values of $\vec{S}$ generating high Laplacian magnitudes are outliers to other possible rescue requests, and hence may be of a particularly high $(++\nabla^2)$ or low $(--\nabla^2)$ priority as compared to a set of other severity configurations. Thus, $\nabla^2$ may provide an impact on priority. In some embodiments, this Laplacian basis of the order equation allows similar rescue requests to be grouped together in the triage order via the relative isolation of outliers, leading to greater efficiency E for such a configuration of $\vec{O}$.

$$\left(\eta_x \cdot \frac{\partial X}{\partial t} + \ldots + \eta_y \cdot \frac{\partial Y}{\partial t}\right):$$

This set of terms encompasses the partial derivative with respect to time of a given function. This term type is beneficially included in the system of equations because factors relating to change over time may be particularly relevant to victim triaging. For example, the rate of change of environmental conditions, or the change in the survival prospects of a given victim in a given scenario.

$(\eta_a \cdot [A+\xi_a] + \ldots + \eta_b \cdot [B+\xi_b])$: This set of terms encompasses scalar values, which have a noise term added to them. This term type is beneficially included in the system of equations, because it allows simple values that possess a degree of uncertainty to be used in an analysis of a victim's predicament. For example, a victim's distance from a nearest hub may have a range of uncertainty attributable to it when the user computing device 110 maintains a velocity above a certain threshold for a sustained period (for example, the victim is running away from a threat).

$$\left(\eta_a \cdot \left[\frac{\partial A}{\partial t} + \xi_a\right] + \ldots + \eta_\beta \cdot \left[\frac{\partial B}{\partial t} + \xi_\beta\right]\right):$$

This set of terms encompasses the partial derivative with respect to time of a given function, also including an additive noise term. This term type is beneficially included in the system of equations, because it allows rates of change that possess a degree of uncertainty to be used in an analysis of a victim's predicament. For example, the success of a given rescue can be impacted by certain environmental factors that change over time, the impact of which can be expressed by a time-series stochastic process based on real-world or simulated data.

$$\left(\eta_{\phi 1} \cdot \left[\xi_{\lambda 1} \cdot \frac{\partial P_1}{\partial t} + \xi_{\lambda 2}\right] + \ldots + \eta_{\phi 2} \cdot \left[\xi_{\lambda 3} \cdot \frac{\partial P_2}{\partial t} + \xi_{\lambda 4}\right]\right):$$

This set of terms encompasses the partial derivative with respect to time of a given function, also including an additive noise term, and a multiplicative noise term. This term type is beneficially included in the system of equations, because it allows rates of change that possess a degree of uncertainty to be used in an analysis of a victim's predicament. Further, the rate of change itself may be subject to a random process, the impact of which is beyond the simple addition of noise. For example, the lifespan of a victim before rescue that changes over time, is subject not only to an addition of noise based on environmental factors, but the basis of the rate itself is subject to multiplicative environmental volatility as survivability is much less predictable as related to any given change of circumstances.

The various Equations and/or terms described in relation to Equations 8.1-8.7 above include stochastic noise terms, $\xi$. In some embodiments, these noise terms, $\xi$, are generated as random values or using a stochastic process, which may be time-discrete or time-continuous. For instance, such a process is a Wiener process or a Brownian motion. The benefit of including these noise terms, $\xi$, is that the noise terms, $\xi$, allow for the unpredictable nature of emergency scenarios to be accounted for, thereby increasing accuracy and reliability of triaging decisions made by the rescue request manger 125.

Within the template of SPDEs of Equations 8.5-8.7, there may exist a need to simplify the Equations to account for or provide ability to use in implementations where computational resources are limited. Hence, in the interest of convergence, deterministic factors $\vec{O}_d$ may be selectively retained over stochastic factors in $\vec{O}_s$. For example, such selection (for example, by the rescue request manager 125) may be made accounting based on simple scalar value terms being deemed of greatest importance, followed by partial derivative terms, and finally by plane Laplacian terms. In some embodiments, the table below provides an example of what terms are of most/least importance, where the least important terms could be eliminated from the computations in environments where computations resources are limited.

| Most Important | S |
| --- | --- |
| | N |
| | R |
| | W |
| | dT |
| | dW |
| | $M_d$ |
| Least Important | $M_r$ |

In some embodiments, triaging algorithms and processes described herein are implemented, at least in part, by calculations of order that may take various factors into account. The influence of these factors is based on the values of different weights on such factors. The exact order equation that results in the most efficient rescue of all victims (for example, which will result in the most lives saved in the least amount of time) is generated by the processes described herein, for example by the rescue request manager 125 and/or the rescue management server 120. The exact order equation may be determined by choosing the weights that are projected to cause the most efficient rescue operation, based, for example, on optimal weights used in past real-world and simulated scenarios.

For example, the order equation may have a specific set of weights $\vec{\eta}$ that are real numbers $\mathbb{R}$. These weights may be applied to respective terms in the order equation to determine the importance of that term, or to remove the term from the order equation. The process for assigning these weights is described in more detail below.

The weights $\vec{\eta}$ meet the following constraints:

Let $\vec{\eta} \mapsto O$ $$\vec{\eta} \subseteq \mathbb{R}^n : \vec{\eta} = [\eta_1 \in \mathbb{R}, \ldots, \eta_n \in \mathbb{R}] \qquad \text{Equation 9}$$

The determination of the weights $\vec{\eta}$ may utilize various functions, etc. In some embodiments, determination of the weights $\vec{\eta}$ may involve implementing a simulation function, $f_{sim}$, that simulates rescue operation scenarios, and which may yield the weights that cause a most efficient rescue operation. The efficiency, E, of the rescue operation may be measured in rescues/hour. The most efficient weight, $\vec{\eta}$, for the order equation is selected by the rescue request manager 125 and/or the rescue management server 120 for the real world scenario $\vec{T}$, which may yield the order equation, $\vec{O}$, for the optimal E.

When $\Omega$ is a collection of set of weights for individual scenarios, the best order equation is determined when those weights are applied and the results sorted by the efficiency value of each scenario's rescue operation when a given acceptable number of victims (i.e. 95%) have been rescued. The first element of this collection, $\Omega$, provides the most efficient weights for the scenario because the value of E is the highest.

The assignment of particular weights, $\vec{\eta}$, to an actual scenario, $\vec{T}$, may be based on prior simulations, $f_{sim}(\vec{M}_d)$. In some embodiments, the determined parameters are generated based on real-world data from an existing situation. Weights, $\vec{\eta}$, may then be assigned by the rescue request manager 125 and/or the rescue management server 120 to a current situations based on previous, similar situations/weights assignments. A rescue operation that takes place in the Scenario $\vec{T}$ may be simulated by $f_{sim}$. The scenario has numerical or function-based parameters that describe its nature (for example, number of victims and responders, location of scenario, weather patterns, hub locations, disaster type and region). Hence, $f_{sim}$ applied to a Scenario $\vec{T}$ generates the most efficient order equation to be used for triaging in that Scenario, based on the most efficient weights for the order equation.

In some embodiments, the simulation function, $f_{sim}$, is a computer-generated time series simulation of the progression of an emergency scenario under the jurisdiction of the rescue request manager 125. The simulation function, $f_{sim}$, may be parametrized with various initial conditions with include, but are not limited to: geographic location, geofences & data overlays, distribution of victims, responders, and responder hubs, and disaster trajectories. In some embodiments, some dimensions or values for these initial conditions are randomly generated.

In some embodiments, the simulation function, $f_{sim}$, evaluates various permutations of weights, $\vec{\eta}$, and measures the efficiency value, E, of the rescue at a given time, t, for the length of the rescue operation. This measurement may be accomplished by applying a given permutation, perm($\vec{\eta}$), to the generation of weights, $\vec{\eta}$, for order equations, $\vec{O}$, for all victims in the computer generated disaster simulation, $f_{sim}$. The permutation of weights, $\vec{\eta}$, that maximizes the efficiency value, E, is used as the optimal set of weights, $\vec{\eta}$, for the parametrized emergency being simulated. In some implementations, the efficiency value, E, is maximized at a point or level set t (for example, at a given time) such that an acceptable number of victims (for example, 95% of the victims) have been rescued to avoid outlier victims detracting from an otherwise efficient choice of weights $\vec{\eta}$.

The permutations of weights, $\vec{\eta}$, are constrained reasonably by previously similar scenarios in the real-world, and those scenarios which have been previously simulated. In some embodiments, machine learning processes identify valid constraints on permutations for weights perm($\vec{\eta}$) given the aforementioned metadata. Such processes can also influence the plane smoothing generation basis of scenarios $M_\mathbb{R}$ in some embodiments.

All of the scenarios that have been encountered before, in the real world, or in simulated trials, may be categorized with titles that are able to be read and understood (for example, "Hurricane in Houston, Tex. on Aug. 25, 2017"). The scenarios are put into such groups (for example, floods, hurricanes, earthquakes) based on k-means or a similar categorization algorithm. This set of scenarios is called the discrete set $M_d$. $M_\mathbb{R}$ is a plane that contains all possible scenarios. This plane is generated from (parameterizations of) scenarios that have occurred in the past. Scenarios can either be discrete (and thus part of the discrete set $M_d$, for example, they have already occurred or have been simulated), or not (and thus part of the plane smoothing $M_\mathbb{R}$ for example, they are based on predictions from scenarios that already took place in some capacity).

Each scenario in $M_d$ is evaluated in such a way such that each scenario point uses the most efficient weights on the order equation for that scenario. This is because the most efficient outcome of each discrete scenario may be used to generate the $M_\mathbb{R}$ plane (at least one step of which may include k-means grouping of the scenarios in $M_d$), such that $M_\mathbb{R}$ is able to approximate the most efficient weights for a new scenario.

In some embodiments, the simulation function, $f_{sim}$, is comprised in part by inference and training processes. For example, $f_{sim}(\vec{T})$ may comprise an inference process of $f_{sim}$, where the best weights, $\vec{\eta}$, is chosen for a scenario, $\vec{T}$, being currently evaluated at runtime. Similarly, $f_{sim}(M_d)$ may comprise a training process for determining the best weights, $\vec{\eta}$, based on weights, $\vec{\eta}$, from past scenarios, $\vec{T}$.

Based on where the current scenario lies on the plane $M_\mathbb{R}$, the weights to be used for order equations in the current scenario are based on the weights from scenario points on the $M_\mathbb{R}$ plane that are in the neighborhood near the current scenario point. The closest approximation of the current scenario point starting at a point on $M_\mathbb{R}$, results in the weights associated with that point being used for the order equations of the current scenario. Discrete scenarios $M_d$ (which are part of the $M_\mathbb{R}$ plane) are preferred for these approximations, unless another point in $M_\mathbb{R}$ is more accurate and suitable.

There are at least two types of training data underlying this process: (1) from past real-world scenarios/disasters/periods of time that were directly handled by the rescue request manager 125; and (2) from simulations of randomly generated disaster scenarios being handled by and/or within the rescue request manager 125, whereas an optimal weight, $\vec{\eta}$, has been identified for maximized efficiency value, E(t), in the scenarios in the discrete set of known scenarios $M_d$. $f_{sim}(M_d)$ may yield a group of scenarios $\vec{T}$ that have the most efficient order equation $\vec{O}$. In other words, $f_{min}(M_d)$ may yield a group of scenarios $\vec{T}$ which are in the most efficient group of weights, order equation, and efficiency value ($<\vec{\eta}, \vec{O}, E>$), providing for the most efficient order equation $\vec{O}$, maximizing efficiency value, E. In some embodiments, a time series $f_{sim}$ is parametrized by an equation for the efficiency value (in this embodiment, characterized by rate of rescues per hour) at a given time $$E(t) = \frac{R_2}{R_1} \cdot 100$$

onto t. The most efficient group of weights, order equation, and efficiency value $\Omega_1$ may be inherent to the parameterization of a scenario $\vec{T}=<p_1, \ldots, p_n>$ passed into $\beta_{min}(\vec{T})$. $\Omega_1$ contains the optimal set of weights for scenario $\vec{T}$.

For example, for each scenario $\vec{T}$ of \the discrete set of scenarios $M_d$, each reasonable permutation of weights $\vec{\eta}$ is compared (with each other) by applying the reasonable permutation of weights $\vec{\eta}$ to the order equation $\vec{O}$ for the scenario $\vec{T}$ being evaluated. In some embodiments, the rescue request manager 125 and/or the rescue management server 120 makes this comparison by measuring the efficiency E at a time t for the given weights $\vec{\eta}$ on the order equation $\vec{O}$ for that scenario $\vec{T}$. The time t may be selected by the rescue request manager 125 and/or the rescue management server 120 such that an acceptable majority of victims (for example, 95%) have been rescued. By sorting the set $\vec{\Omega}$ by descending efficiency values, the set $\Omega_1$ containing weights on the order equation that cause the highest efficiency value can be identified and/or selected.

In some embodiments, the rescue request manager 125 and/or the rescue management server 120 may infer the optimal weights for current scenario based on both the discrete set of scenarios $M_d$ and the plane smoothing set of scenarios $M_\mathbb{R}$. These two sets may provide two different initial conditions that are used to approximate the current scenario $\vec{T}$ via, for example, gradient descent. This inference process uses prior scenarios in both sets that are in the same $\mathbb{R}^n$ neighborhood as the current scenario and infers optimal weights for the current scenarios based on the values of weights for prior scenarios in the neighborhood.

In some embodiments, coordinate points on the plane $M_\mathbb{R}$ are in fact vectors $\vec{\Gamma}$. From nearby $\vec{\Gamma}$ (i.e. points in the same neighborhood on the plane), $\vec{\eta}$ can be inferred by the rescue request manager 125 and/or the rescue management server 120. The $\vec{\Gamma}$ being plotted for $M_\mathbb{R}$ are $\Omega_1$. Hence, the new $\vec{\Gamma}$ is $\Omega_1$ as well, by plane neighborhood inference via gradient descent or a similar process, depending on the implementation.

In some implementations, the above process for selecting weights can be applied similarly to: $\vec{\eta}$ determination for time step n described herein; internal $\vec{\eta}$ of routing coefficient described herein; $\vec{\eta}$ determination for S described herein; and $\vec{\eta}$ generation for simpler equations, such as V* described herein.

As noted above, one important consideration for the rescue request manager 125 is triaging victim rescue requests based on the severity of each victim's specific request. If one victim's rescue request provides that their predicament is more severe than that of another victim, the victim with a greater severity score will be ordered or prioritized to be rescued first. The severity score may provide a fundamental measure that rescue requests are measured against, and which correlates with established EMS/PD or similar codes that provide first responders with critical information about victims. Equation 8 below provides an example regarding how victim severity scores are calculated and/or quantified by a magnitude of a weighted, vector valued function S.

$$S: \mathbb{R}^N \to \mathbb{R}$$

$$S = \|<\eta_1 \cdot f_1, \ldots, \eta_n \cdot f_n>\| = \|\vec{\eta} \cdot \vec{f}\| \quad \text{Equation 10}$$

In Equation 9, the $\eta$ values represent weights applied to components of the functions $f$ that lead to the severity score, S. These weight terms may ascribe certain importance to particular components of S. Details of the weights are provided herein. Examples of the functions $f$ may include EMS/PD codes or tiers or output of a function applied onto these codes, victim distance from responders, victim battery life, network factors, and so forth. Each factor may be a general factor contributing to a victim's severity score, S. Each function can take the form of a vector, a scalar, a partial differential equation (PDE), a machine learning algorithm, and/or other function types yielding a result that assists in determining the severity of a victim's predicament based on their rescue request.

The terms of S may have weights $\eta$ because the importance of terms of S in the vector generation basis are (a) predetermined by a human managing authority of the rescue request manager 125 or, depending on the embodiment, (b) the importance of different factors of S that may be determined by machine learning techniques applied to data of previous rescue requests or through another optimization process.

Overview of Example Rescue Application User Interfaces

Figure 4A:
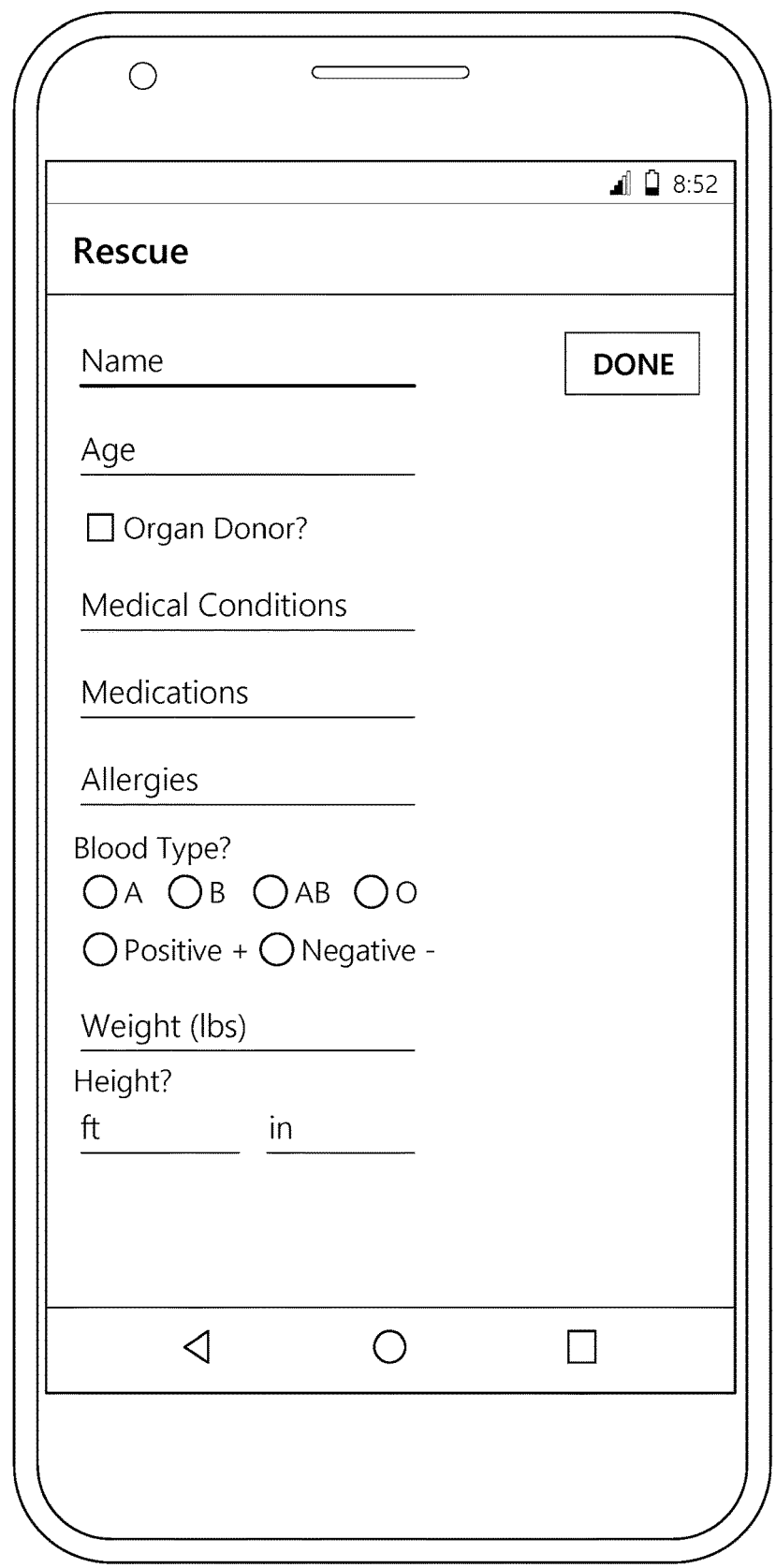
FIGS. 4A and 4B depict example graphical user interfaces relating to pre-stored data in the rescue application of FIGS. 1A and 1B.
Figure 4B:
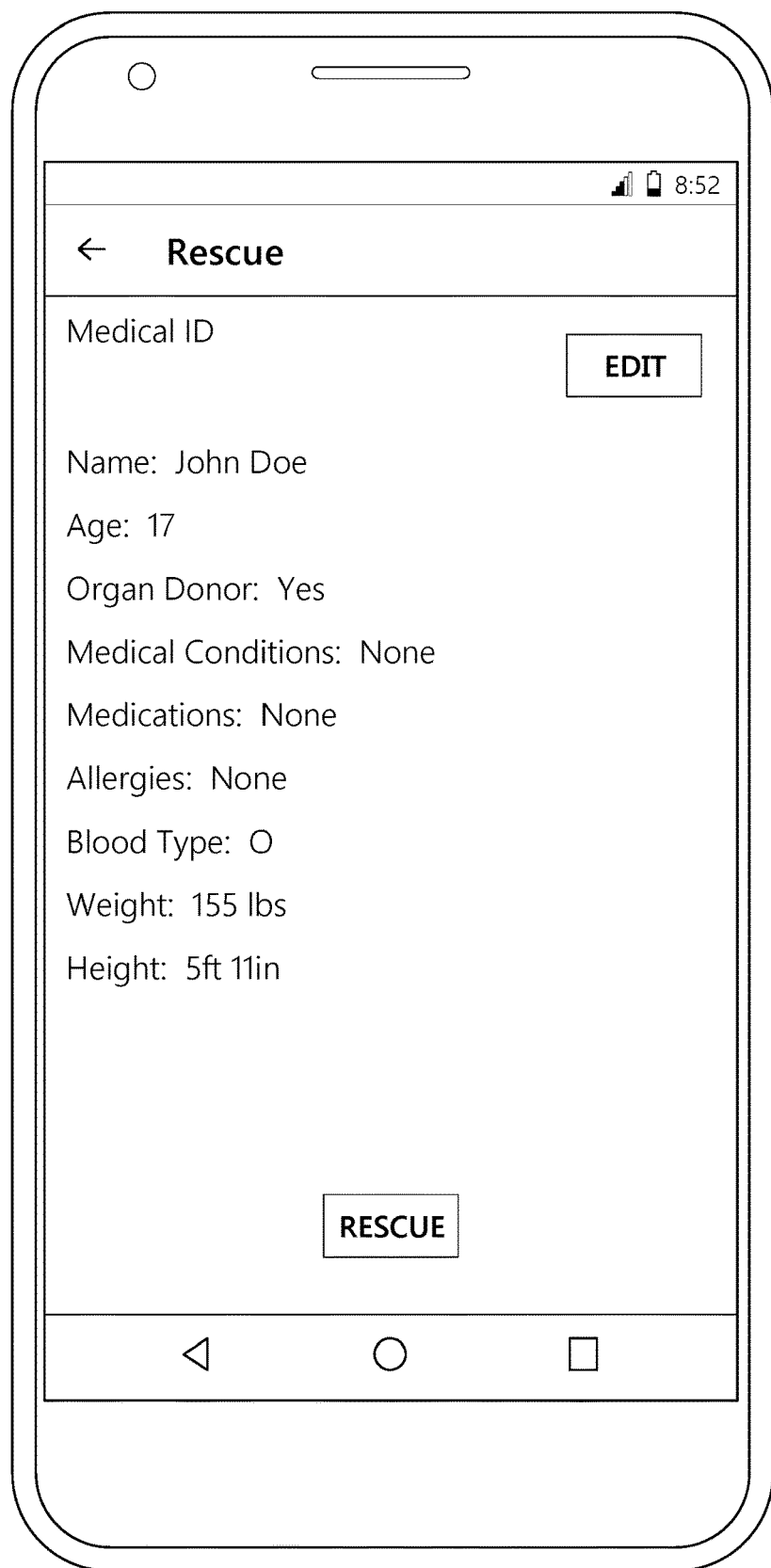

FIGS. 4A and 4B depict example graphical user interfaces relating to pre-stored data in the rescue application 105. Specifically, FIG. 4A depicts a user interface that prompts a user to enter in certain medical information that may be relevant to a future (or current) rescue request, and FIG. 4B depicts a visual representation of the information that can be pre-stored based on user input into the user interface of FIG. 4A. The user interface of FIG. 4A may be presented to a user in advance of any emergency rescue request, for example when the user initially configures the rescue application 105. As depicted, the medical information can include the name, age, organ donation status, medical conditions, medications, allergies, blood type, weight, and height of the user. Beneficially, pre-storing this information increases the speed with which the user can transmit a rescue request including their medical information to the emergency response system 100. In some embodiments, this medical information may be present in another application on the user computing device 110, and the rescue application 105 may pull the data from that application. As will be appreciated, medical information can be stored and transmitted by the rescue application 105 in compliance with medical data privacy regulations and associated protocols.

Figure 5A:
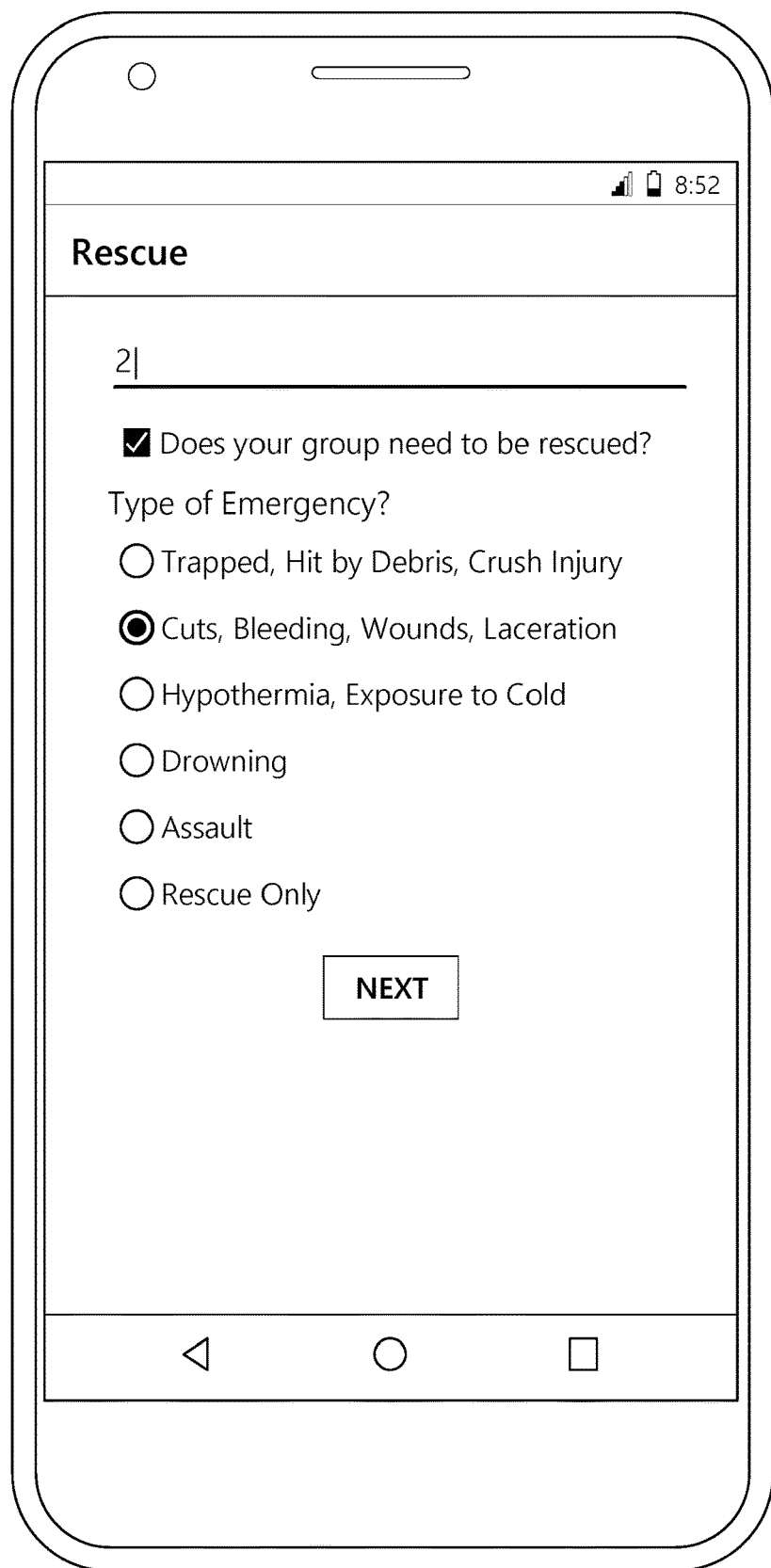
FIG. 5A depicts an example graphical user interface for initiating a rescue request in the rescue application of FIGS. 1A and 1B.

FIG. 5A depicts an example graphical user interface for initiating a rescue request in the rescue application 105. FIG. 5A represents one example of an initial user interface that enables the user to select which type of emergency they are experiencing. The initial user interface allows the user to specify how many people are in their group and whether their group needs to be rescued, and then allows the user to select from one of several pre-defined types of emergencies. Although FIG. 5A lists several options, it will be appreciated that these options can be modified and/or reordered as described herein. The example types of emergencies of FIG. 5A include (1) trapped, hit by debris, crush injury, (2) cuts, bleeding, wounds, laceration, (3) hypothermia, exposure to cold, (4) drowning, (5) assault, and (6) rescue only. Emergency types (1)-(5) were selected based on a set of most commonly occurring codes in existing EMS codes. EMS codes refer to the existing codes used by emergency services to classify incoming emergency calls and dispatch field units. These codes may be organized as a hierarchy by the disclosed emergency response system 100, such that codes relating to specific injuries and emergency scenarios would be organized under a more general code for a type of emergency. Emergency type (6) may provide a rapid way for a user to request rescue without having to provide further information, and selection of this option may trigger transmission of the request.

FIGS. 5B-5F depict example follow-up graphical user interfaces for providing further emergency scenario details in the rescue application of FIGS. 1A and 1B. The follow-up user interfaces can include menus and selectable options relating to more specific details of the emergency types in the user interface of FIG. 5A in order to efficiently obtain a complete package of information regarding the nature of the emergency from the user. Each selectable option may be associated with a certain point score that is used to calculate the severity score representing the severity of the emergency and likelihood of survival. These point scores may not be exposed to the user to prevent tampering with prioritization of requests. Any text input into free-form fields may be analyzed, for example by natural language processing techniques, in order to determine whether the rescue request is associated with the correct EMS code.

Figure 5B:
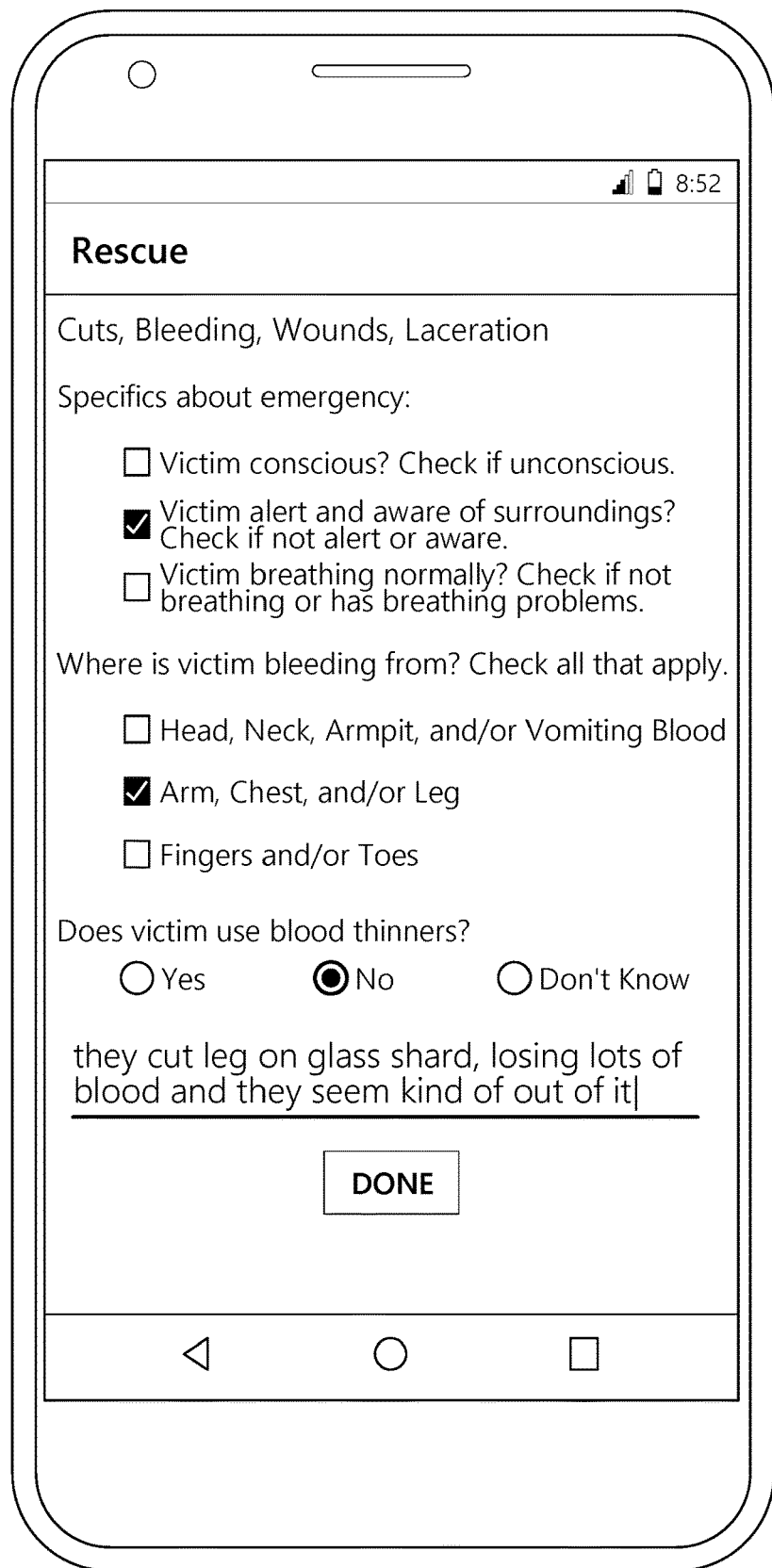
FIGS. 5B-5G depict example follow-up graphical user interfaces for providing further emergency scenario details in the rescue application of FIGS. 1A and 1B.

FIG. 5B depicts a follow-up user interface that is displayed responsive to user-selection of the "cuts, bleeding, wounds, laceration" emergency type in the initial user interface of FIG. 5A. The user interface of FIG. 5B includes a first set of menu options for assessing the severity of the emergency, including options to indicate whether the victim is unconscious, whether the victim is not alert/aware of their surroundings, and whether the victim is having difficulty breathing. The user interface of FIG. 5B includes a second set of menu options for describing the wound of the victim, including indicating a location of the bleeding. Alternative user interfaces may enable the user to draw the location and size of the cut or cuts on a representation of the human body. The user interface also checks whether the victim users blood thinners and enables a free-form text input for provision of further details.

Figure 5C:
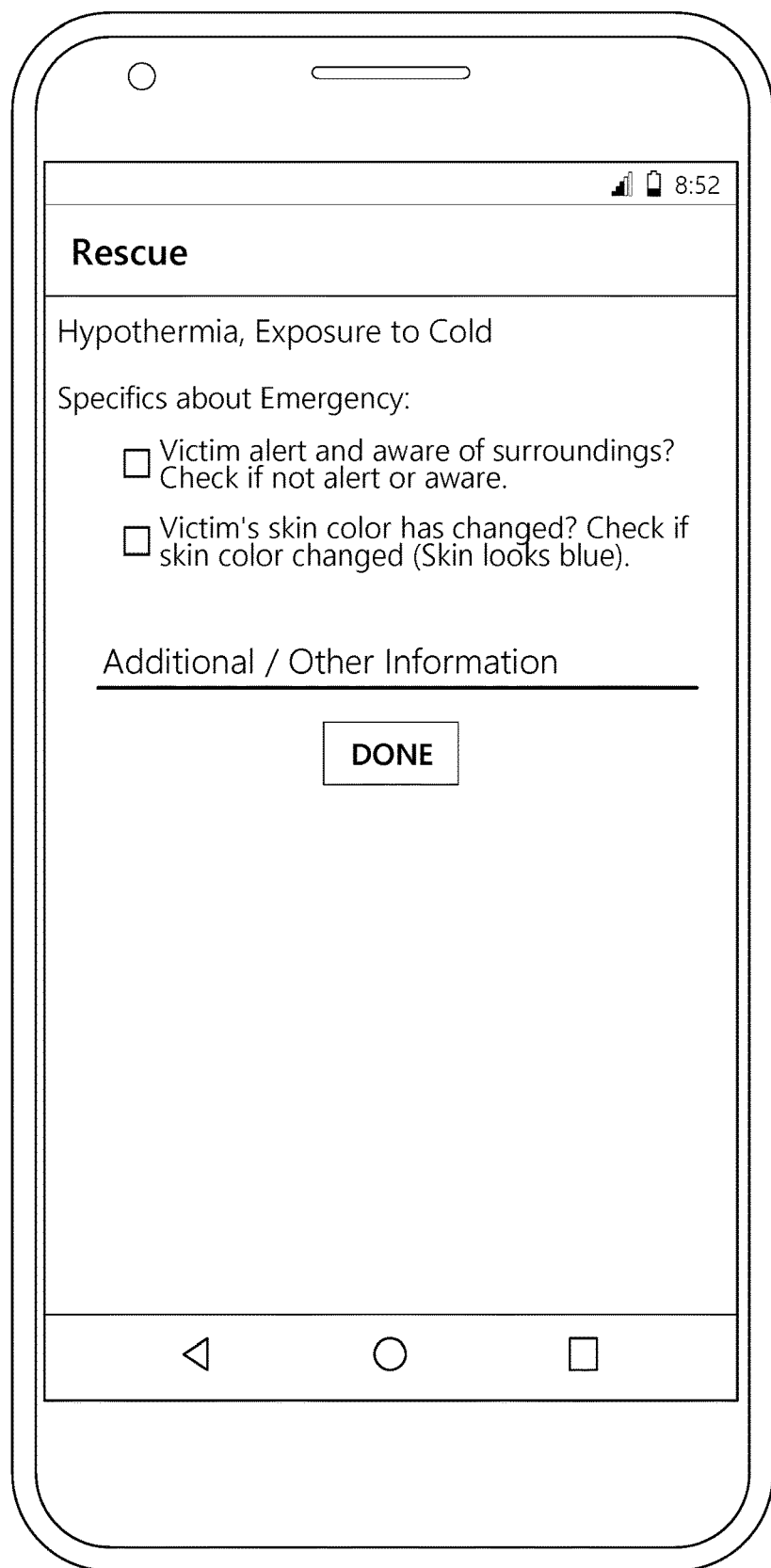

FIG. 5C depicts a follow-up user interface that is displayed responsive to user-selection of the "hypothermia, exposure to cold" emergency type in the initial user interface of FIG. 5A. The user interface of FIG. 5C includes a set of menu options for assessing the severity of the emergency, including options to indicate whether the victim is not alert/aware of their surroundings and whether the victim's skin color has changed. Other examples can include menu options to indicate whether the victim is unconscious or having difficulty breathing. The user interface of FIG. 5C also includes a free-form text input for provision of further details.

Figure 5D:
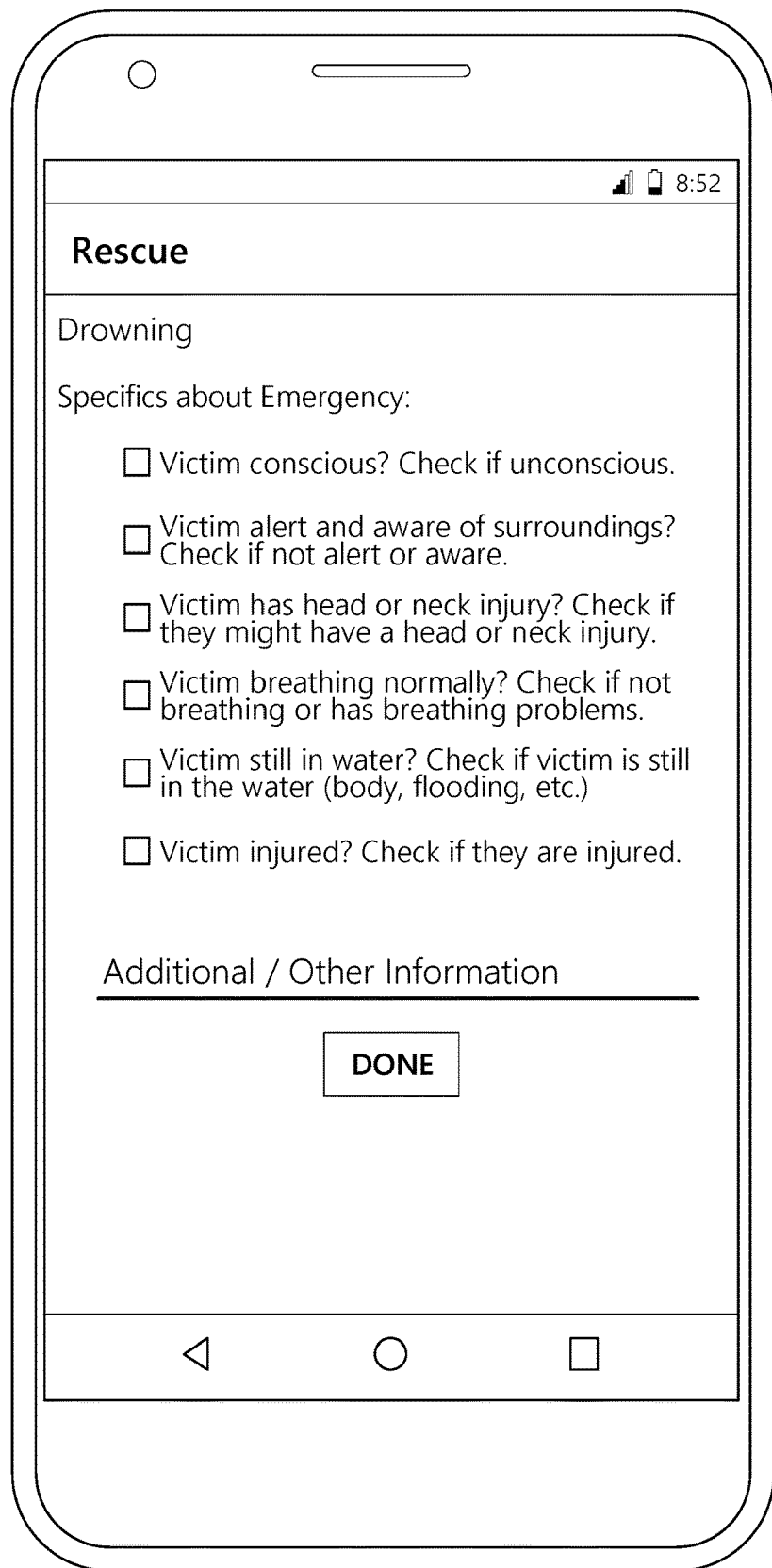

FIG. 5D depicts a follow-up user interface that is displayed responsive to user-selection of the "drowning" emergency type in the initial user interface of FIG. 5A. The user interface of FIG. 5D includes a set of menu options for assessing the severity of the emergency, including options to indicate whether the victim is unconscious, whether the victim is not alert/aware of their surroundings, whether the victim has a head or neck injury, whether the victim is having difficulty breathing, whether the victim is still in the water, and whether the victim is injured. The user interface of FIG. 5D also includes a free-form text input for provision of further details. If the user selects the option to indicate that the victim is injured, this may prompt the rescue application 105 to display an additional user interface to obtain details about the injury, for example the user interface of FIG. 5B. Some implementations may include a selectable option to indicate whether the drowning also involves exposure to cold, which may trigger the rescue application 105 to display the user interface of FIG. 5C.

Figure 5E:
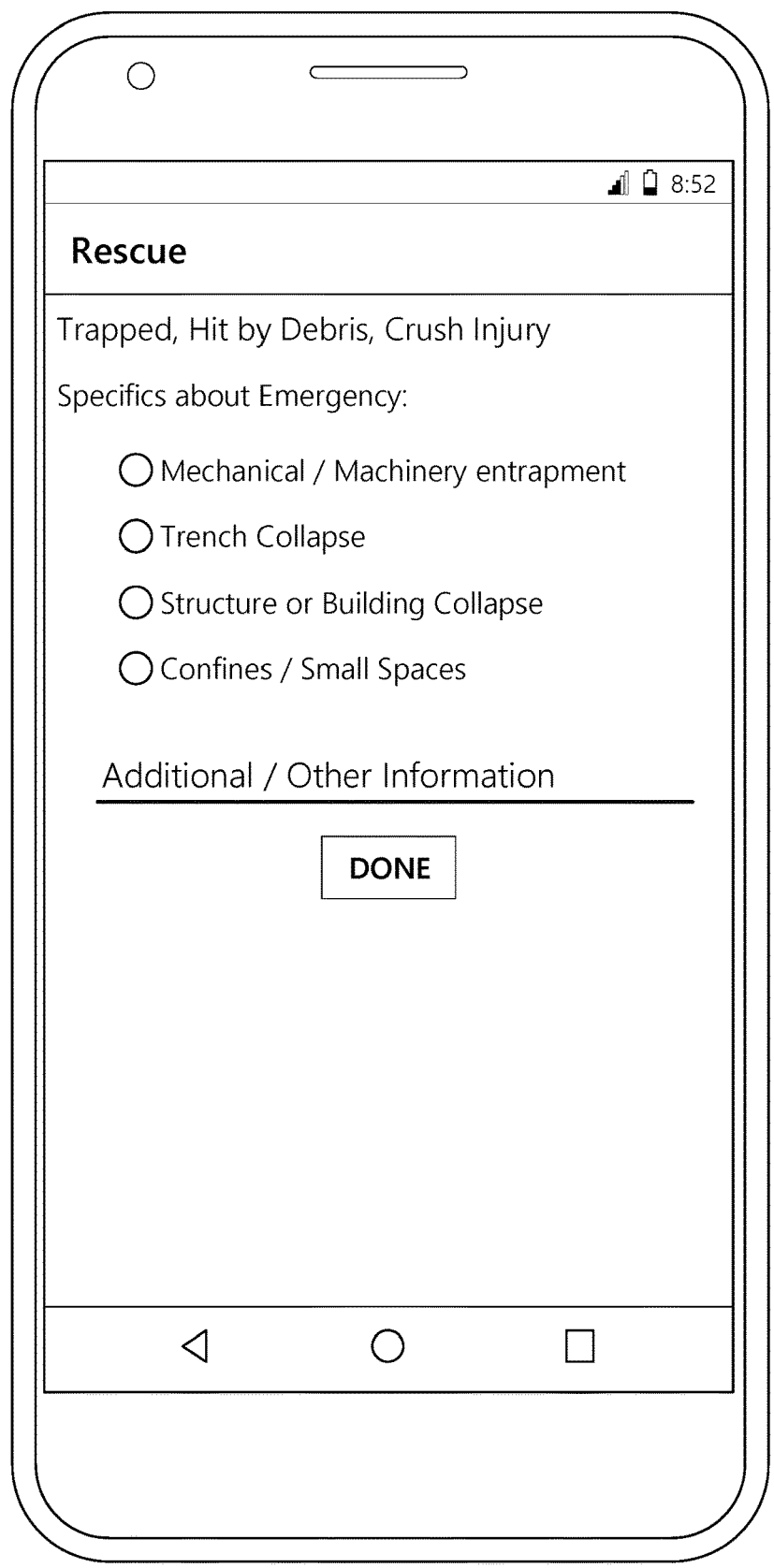

FIG. 5E depicts a follow-up user interface that is displayed responsive to user-selection of the "trapped, hit by debris, crush injury" emergency type in the initial user interface of FIG. 5A. The user interface of FIG. 5E includes a set of menu options for assessing the severity of the emergency, including options to indicate whether the emergency relates to mechanical or machinery entrapment, trench collapse, structure or building collapse, or a confined/small space. Other examples can include menu options to indicate whether the victim is unconscious, not aware of their surroundings, or having difficulty breathing. The user interface of FIG. 5E also includes a free-form text input for provision of further details. Some implementations may include a selectable option to indicate whether the entrapped victim has any injuries, which may trigger the rescue application 105 to display an additional user interface to obtain details about the injury, for example the user interface of FIG. 5B.

Figure 5F:
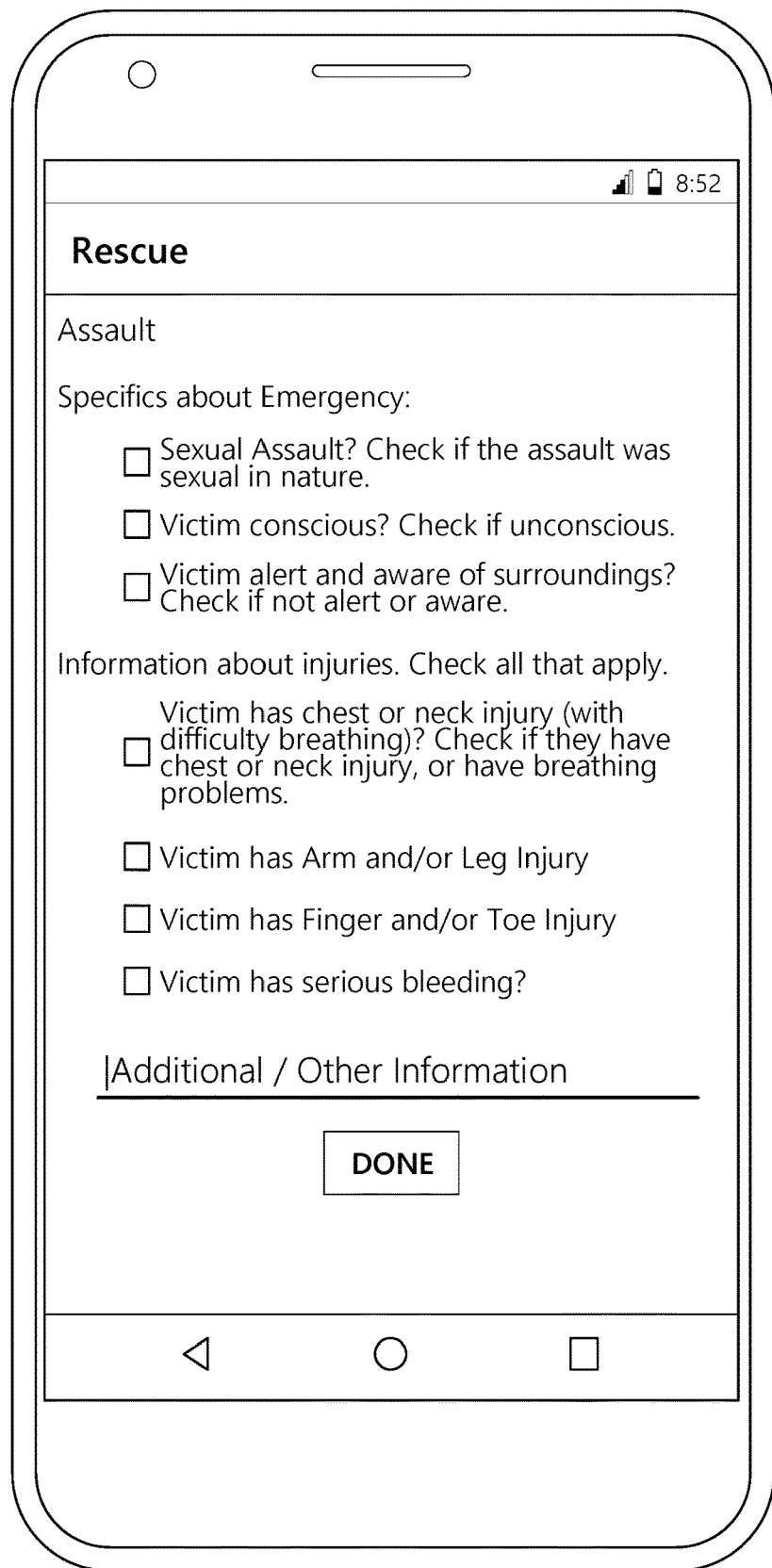

FIG. 5F depicts a follow-up user interface that is displayed responsive to user-selection of the "assault" emergency type in the initial user interface of FIG. 5A. The user interface of FIG. 5F includes a first set of menu options for assessing the severity of the emergency, including options to indicate whether the assault is a sexual assault, whether the victim is not unconscious, and whether the victim is not alert/aware of their surroundings. The user interface of FIG. 5F includes a second set of menu options for describing the injuries of the victim, including indicating a location of injuries and whether the victim has serious bleeding. Selection of the injury-related menu options may trigger the rescue application 105 to display an additional user interface to obtain details about the injury, for example the user interface of FIG. 5B. The user interface of FIG. 5F also includes a free-form text input for provision of further details.

In some implementations, the rescue request manager 125 can be configured to associate specific types of emergency dispatch personnel with specific ones of the emergency types in the initial menu. Further, the rescue request manager 125 can be configured to use the menu selections relating to emergency severity in order to assign a severity score used during triage of the rescue request. The selections relating to emergency severity can additionally be used by the rescue request manager 125 to determine which emergency responders are appropriate for the particular emergency of a given rescue request, and/or to alert designated emergency responders as to specific equipment or personnel that should be included in the dispatch. The rescue request manager 125 may parse any text provided in free-form input fields for use in assessing emergency severity and/or suitable emergency responders, for example using natural language processing, and/or may pass on the text to the dispatched emergency responder.

Figure 5G:
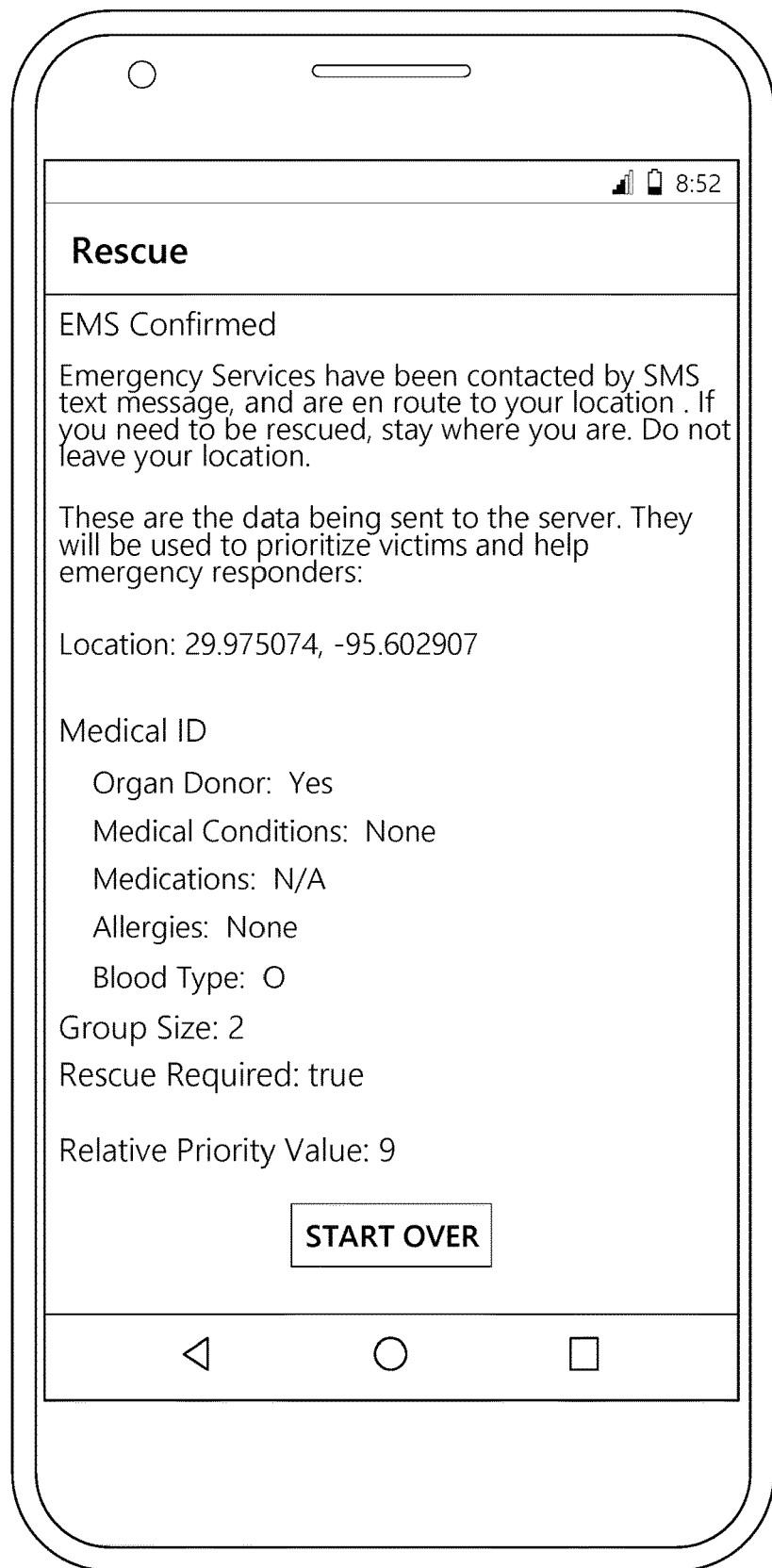

FIG. 5G depicts an example user interface for confirming to the user that emergency services have been provided with their rescue request. The example confirmation user interface indicates the user's location, their pre-stored medical information transmitted with the request, their group size, and the priority of their request. Other implementations may display more or less information, or may simply display a confirmation message. It may be desirable to not display the relative priority value to users in order to conceal the criteria used to generate severity scores, in order to prevent willful tampering with rescue priorities. Some implementations may include a selectable option enabling the user to additionally call an emergency rescue number if the further desire to speak to PSAP agent. In some implementations, the user interface of FIG. 5G can be updated when emergency responders are provided with the rescue request, and can be further updated with status information regarding dispatched responders while en-route.

Overview of Example Emergency Response System Simulation

Figure 6:
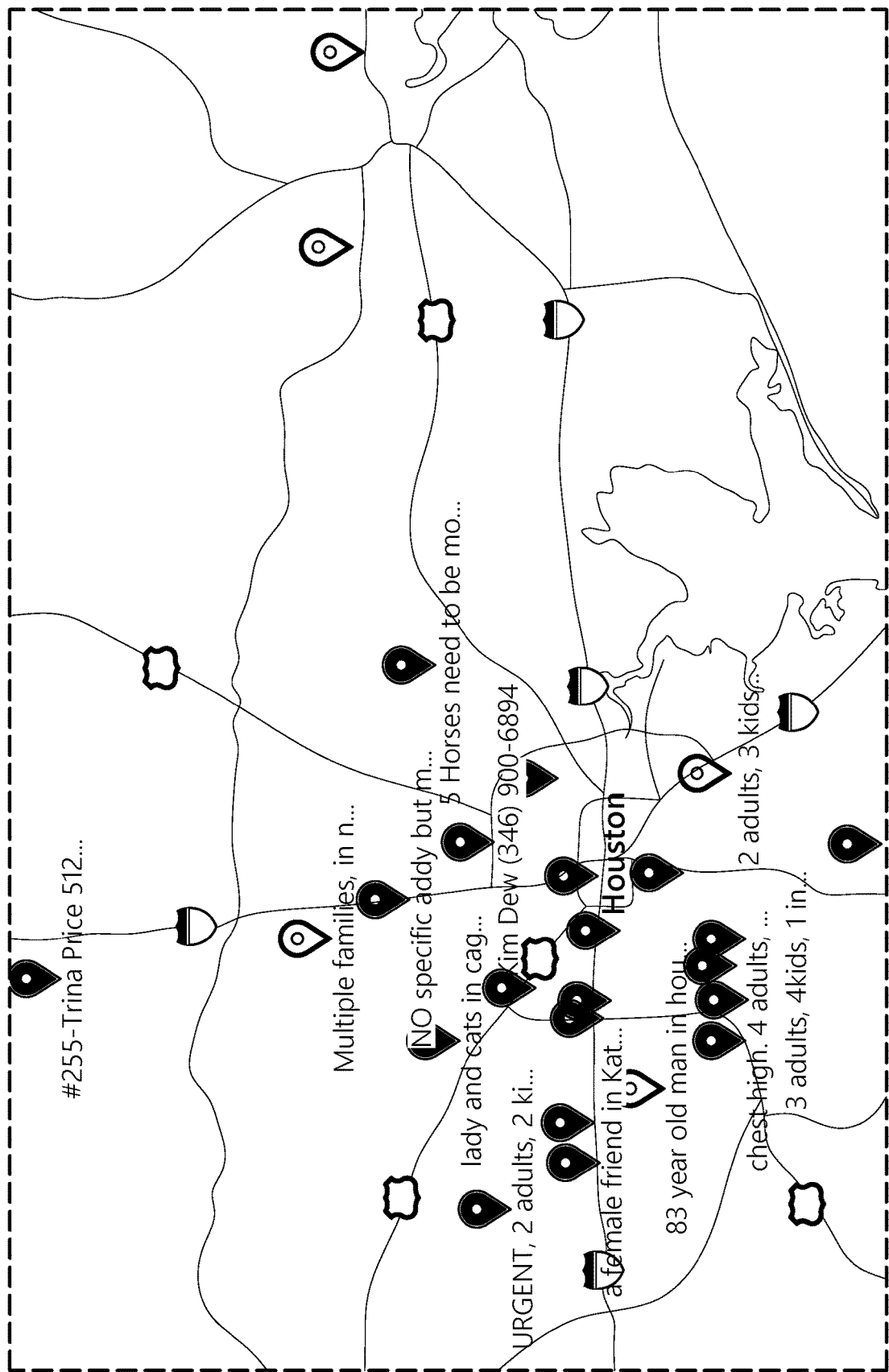
FIG. 6 depicts a map of emergency request locations in a simulation of the emergency response system of FIG. 1A.

FIG. 6 depicts a map of emergency request locations in a simulation of the rescue operations that could have been coordinated by the emergency response system 100 during a past real-life disaster emergency: Hurricane Harvey.

The map shown in FIG. 6 reflects a mapping made by rescue teams based on social media posts requesting assistance after 9-1-1 was overloaded. That mapping was used to rescue hundreds of families during the hurricane.

The simulation run to test the efficiency of the emergency response system 100 used 197 real-life data points from the map (shown in red), and generated 20 more data points (shown in blue) in random locations to simulate mobile phones that failed to provide data other than location and pre-provided information (e.g., the user does not use the rescue application 105 to contact the server). These 217 points are tested as groups of 4 people, representing an average of individuals and large households that needed rescue during the hurricane. The simulation modeled using 21 simulated emergency responders working out of the three largest shelter hubs that were used during Hurricane Harvey.

Efficiency of the simulation was modeled using the following equation:

$$E = 1 - R2/R1 \qquad \text{Equation 11}$$

where E=efficiency, measured as % change from R1 to R2; R1=first rescue rate; and R2=second rescue rate.

Efficiency, E, constitutes improvements the rescue rate R, which is measured in rescues per hour. Coast Guard Data suggests their rescue rate R during Hurricane Harvey was approximately 7.03 rescues per hour for a 72 hour operation. The average operation time in the simulations was 13.77 hours, assuming an average rescue vehicle speed of 22 miles per hour, yielding R=15.8 rescues per hour. Taking into account responder vehicle velocity, capacity, and distance traveled, a Hurricane Harvey-type rescue operation supplemented by use of the disclosed emergency response system 100 could be 122.4% more efficient.

Figure 7:
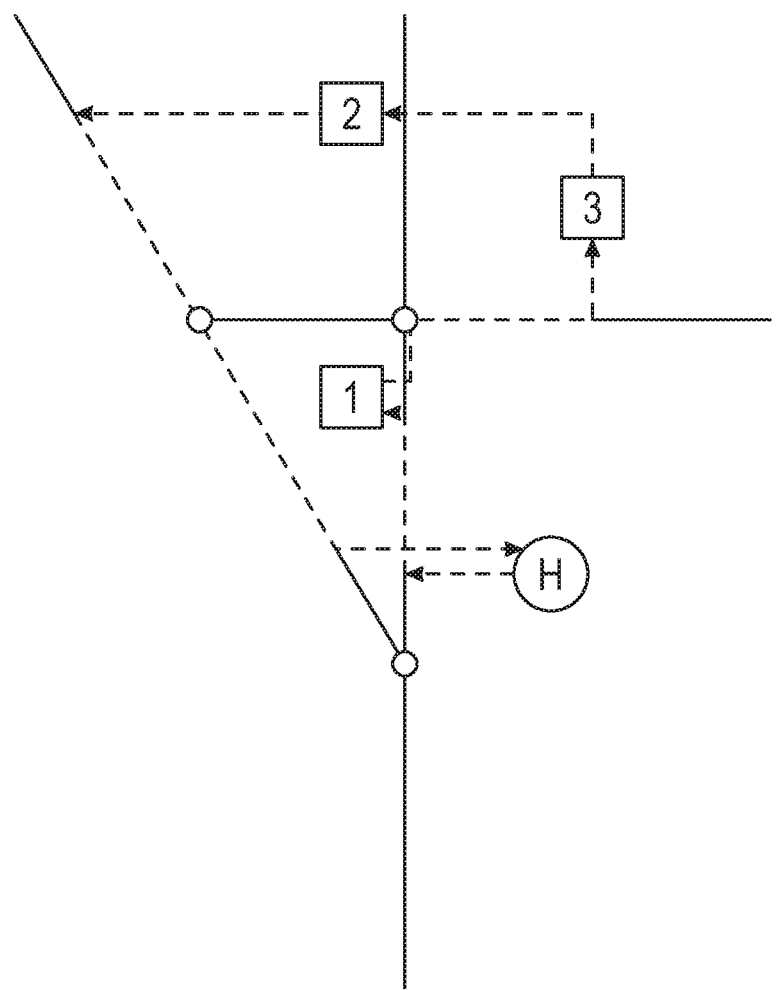
FIG. 7 depicts a simplified route taken by emergency responders when not impeded by a disaster area.

FIG. 7 depicts a simplified route taken by emergency responders when not impeded by a disaster area. For each of FIGS. 7-9, The route traversed by the emergency responders is shown with the dashed line. The solid lines shown represent highways traveled by the emergency responders. Where the dashed lines appear to overlap with solid lines, the emergency responders are interpreted to travel along the highways. Where the dashed lines are shown between solid lines and one of a hub, H, victim 1, victim 2, and victim 3, the emergency responders are determined to travel on inner roads or roads that are not highways. In some embodiments, highways are determined to be more efficient to travel than inner roads.

As shown in FIG. 7, the emergency responders travel from the hub, H, along a first combination of a first highway and at least one first inner road to victim 1. The emergency responders then travel from the victim 1 to the victim 2 along a second combination of the first highway, a second highway, and at least one second inner road. The emergency responders then travel from the victim 2 to the victim 3 along a third combination of inner roads. Finally, the emergency responders then travel from the victim 3 to the hub, H, along a fourth combination of inner roads and a third highway.

Figure 8:
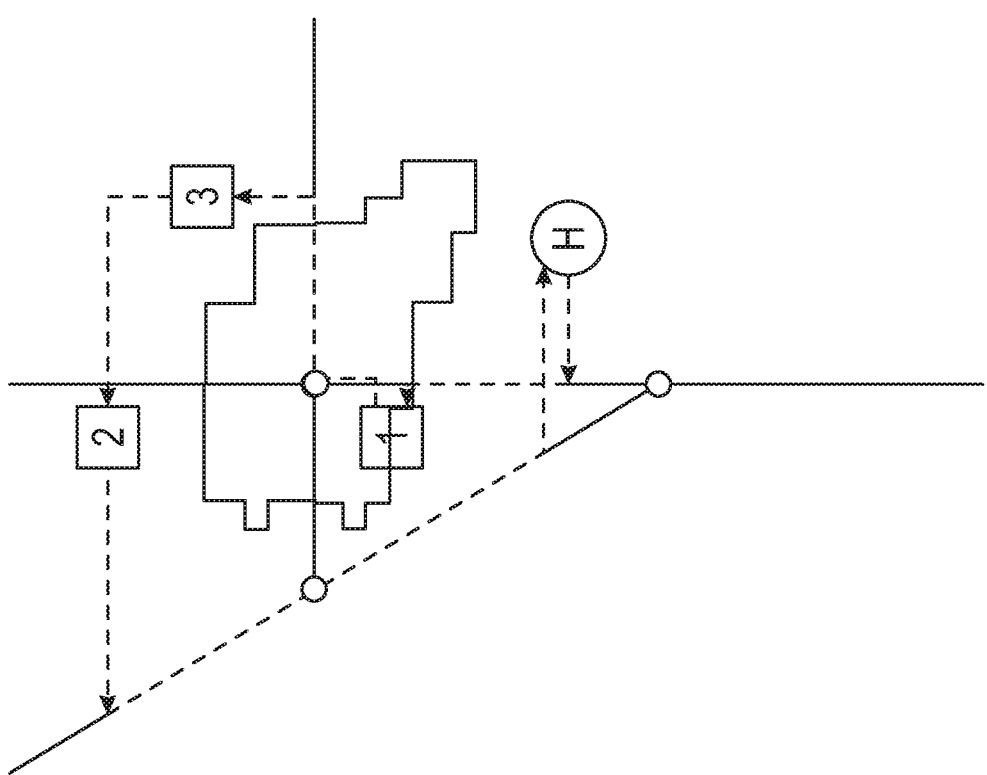
FIG. 8 depicts the simplified route of FIG. 7 with a disaster area overlaid that impedes at least one portion of the simplified route.

FIG. 8 depicts the simplified route of FIG. 7 with a disaster area overlaid that impedes at least one portion of the simplified route. Thus, the emergency responders may be unable to travel the route from FIG. 7 because the disaster area may introduce dangers, delays, or other issues that make the route of FIG. 7 less efficient than one or more other routes.

The route traversed by the emergency responders is shown with the dashed line. The solid lines shown represent highways traveled by the emergency responders. Where the dashed lines appear to overlap with solid lines, the emergency responders are interpreted to travel along the highways. Where the dashed lines are shown between solid lines and one of a hub, H, victim 1, victim 2, and victim 3, the emergency responders are determined to travel on inner roads or roads that are not highways. In some embodiments, highways are determined to be more efficient to travel than inner roads.

As shown in FIG. 7, the emergency responders travel from the hub, H, along a first combination of a first highway and at least one first inner road to victim 1. The emergency responders then travel from the victim 1 to the victim 3 along a second combination of the first highway, a second highway, and at least one second inner road. The emergency responders then travel from the victim 3 to the victim 2 along a third combination of inner roads. Finally, the emergency responders then travel from the victim 2 to the hub, H, along a fourth combination of inner roads and a third highway.

Figure 9:
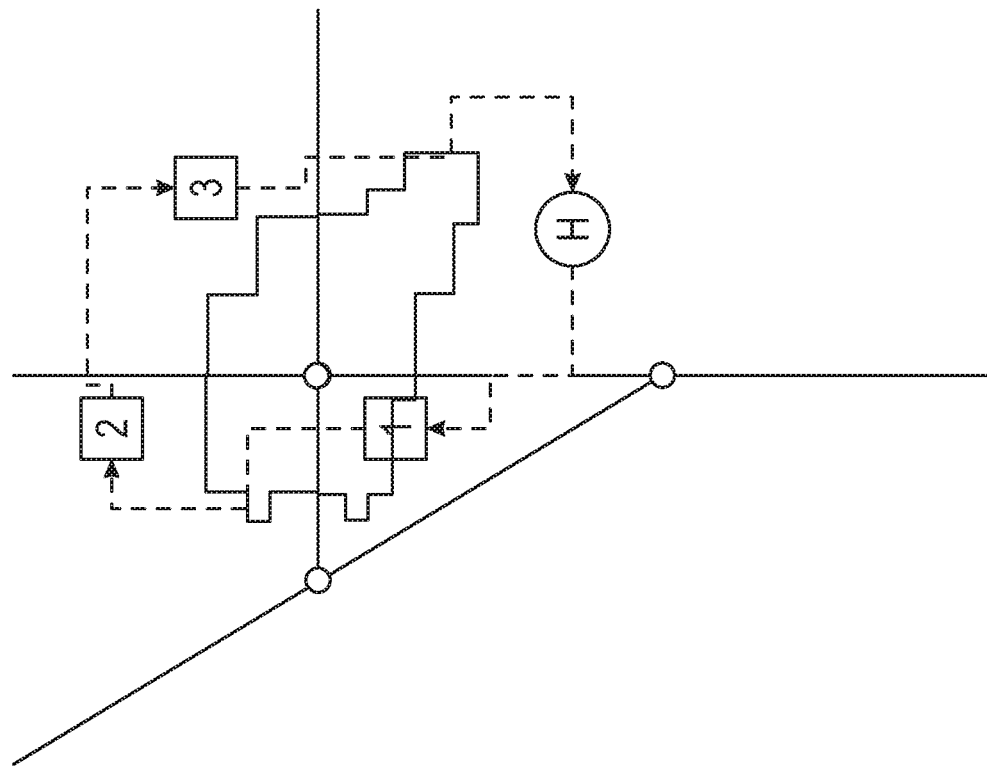
FIG. 9 depicts how a modified route is generated to substantially avoid traversing the disaster area along the simplified route.

FIG. 9 depicts a modified route generated to substantially avoid traversing the disaster area along the simplified route. As shown in FIG. 9, the emergency responders travel the modified route from the hub, H, along a fifth combination of a first highway and at least one first inner road, different from the first combination, to victim 1. The emergency responders then travel from the victim 1 to the victim 2 along a fifth combination at least one inner road. The emergency responders then travel from the victim 2 to the victim 3 along a sixth combination of inner roads. Finally, the emergency responders then travel from the victim 3 to the hub, H, along a seventh combination of inner roads. As compared to the simplified route in FIG. 7, the modified route may substantially avoid traveling into and/or through the disaster area and visits the victims in a different order. In some embodiment, the modified route may be generated by the rescue management servers 120 and/or the rescue request manager 125 in response to rescue requests in and/or around the disaster area according to the methods and/or processes described herein.

Figure 10:
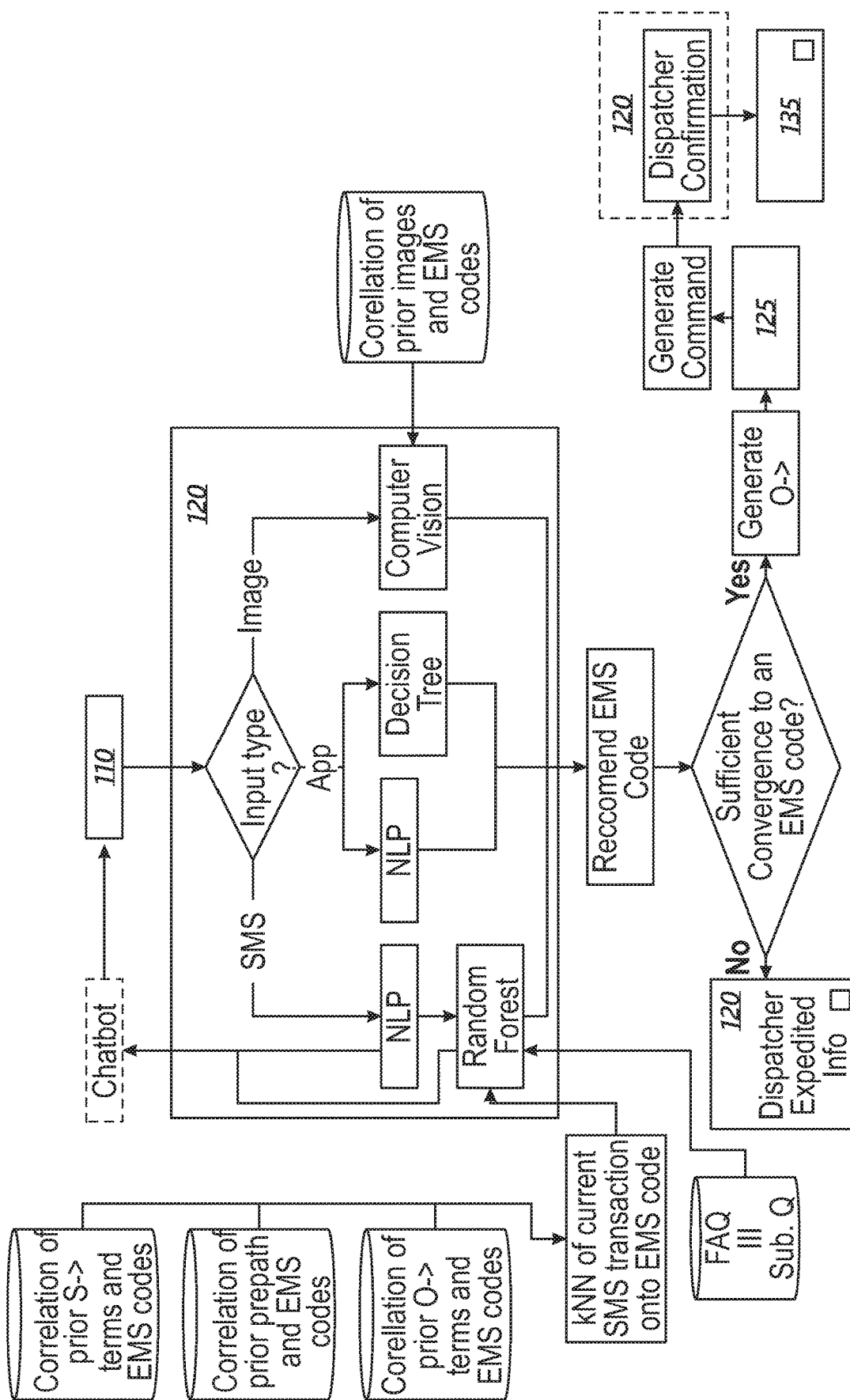
FIG. 10 is a flowchart of how inputs from the user computing device of FIG. 1 is handled by the rescue management server.

FIG. 10 is a flowchart of how inputs from the user computing device of FIG. 1 is handled by the rescue management servers 120. As shown, a user computing device 110 provides an input to the rescue management servers 120 that is one of: (1) an SMS message, (2) a data packet from a mobile app, and/or (3) image or video file.

When the input is an SMS message, the input is evaluated using natural language processing (NLP). For example, the text may be translated from another language, sentiment may be determined, and quantitative features such as victim location and type of injury may be extracted. The data provided is analyzed with random forest to attempt to converge on an EMS code. In some cases, a chatbot application solicits 110 for at least one more piece of information, where the question that the chatbot asks the victim is at least in part influenced by the random forest. The questions that the above chatbot asks the victims come from a bank of Substantial Questions that are used to converge on an EMS code. The random forest itself is constructed in part by k Nearest Neighbor grouping of the features of the current SMS transaction onto a given EMS code. This grouping is, in turn, based on (a) the correlation of prior severity vector terms and EMS codes, (b) the correlation of the prior prepaths (i.e. the sequence of which Substantial Questions were asked and in what order) and EMS codes, and (c) the correlation of prior order equation terms and EMS codes.

When the input is a data packet from the mobile app (for example, the rescue request packet described herein, the input may be evaluated using natural language processing. For example, the text may be translated from another language, sentiment may be determined, and additional quantitative features such as further information regarding type of injury may be extracted. Simultaneously, the victim navigates a set of options (a decision tree) that converge upon an EMS code, with the aforementioned features of natural language processing also being taken into account in this process.

When the input includes an image, video, and other such media, the media may first be subjected to computer vision analysis, wherein features relevant to the determination of EMS code, such as weapons detection and/or injury analysis are extracted. This computer vision process may be based on a data set that correlates prior images with features and victim EMS codes.

Finally, these three (1, 2, 3) pathways are analyzed to recommend an EMS code, based on the statistical confidence of each process of analysis. If there is sufficient convergence to an EMS code (for example, confidence is high enough in the suggestion(s)), the features extracted from the above processes are used to construct the value of an order equation within the rescue request manager 125. The rescue request manager 125 proceeds to generate a rescue command that is delivered to the responder application 135. An optional step exists for dispatchers to approve such commands once generated (for example, in some embodiments, confidence greater than or equal to 80% may be acceptably convergent but require responder approval, but confidence above 95% can be immediately dispatched without human approval, such as the PSAP agent). It follows that if there is not sufficient convergence to an EMS code, then the PSAP agent may be forwarded a concise and expedited packet of information relating to the victim from 120 for analysis. At this point, the PSAP agent may complete the extraction of data and dispatch of responders for the victim.

Terminology

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, or may be implemented in application-specific circuitry of the computer system. Where the computer system includes multiple computing devices, these devices may, but need not, be co-located. The results of the disclosed methods and tasks may be persistently stored by transforming physical storage devices, such as solid-state memory chips or magnetic disks, into a different state. In some embodiments, the computer system may be a cloud-based computing system whose processing resources are shared by multiple distinct business entities or other users.

The processes may begin in response to an event, such as on a predetermined or dynamically determined schedule, on demand when initiated by a user or system administer, or in response to some other event. When the process is initiated, a set of executable program instructions stored on one or more non-transitory computer-readable media (e.g., hard drive, flash memory, removable media, etc.) may be loaded into memory (e.g., RAM) of a server or other computing device. The executable instructions may then be executed by a hardware-based computer processor of the computing device. In some embodiments, the process or portions thereof may be implemented on multiple computing devices and/or multiple processors, serially or in parallel.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, computer software that runs on computer hardware, or combinations of both. Moreover, the various illustrative logical blocks and modules described in connection with the embodiments disclosed herein can be implemented or performed by a machine, such as a processor device, a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements or steps. Thus, such conditional language is not generally intended to imply that features, elements or steps are in any way required for one or more embodiments or that one or more embodiments necessarily include logic for deciding, with or without other input or prompting, whether these features, elements or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, or Z). Thus, such disjunctive language is not generally intended to, and should not, imply that certain embodiments require at least one of X, at least one of Y, and at least one of Z to each be present.

While the above detailed description has shown, described, and pointed out novel features as applied to various embodiments, it can be understood that various omissions, substitutions, and changes in the form and details of the devices or algorithms illustrated can be made without departing from the scope of the disclosure. As can be recognized, certain embodiments described herein can be embodied within a form that does not provide all of the features and benefits set forth herein, as some features can be used or practiced separately from others. All changes which come within the meaning and range of equivalency of the claims are to be embraced within their scope.

What is claimed is:

1. An emergency response system, comprising:
    first computing device comprising one or more first processors programmed to execute instructions that cause at least one first processor of the one or more first processors to generate a first rescue request packet based on emergency information provided by a user;
    at least one server comprising one or more second processors programmed to execute instructions that cause at least one second processor of the one or more second processors to:
        receive a plurality of rescue request packets from a plurality of computer devices, including the first rescue request packet from the first computing device,
        receive one or more geofencing factors from at least one of the plurality of rescue request packets,
        identify a plurality of rescue requests from the plurality of rescue request packets, each rescue request corresponding to one of the rescue request packets and providing details regarding a respective victim, respective emergency conditions based on respective emergency information, and respective computing device information including a battery life of a respective computing device,
        triage each of the rescue requests to generate an order according to which the respective victims are to be rescued, wherein each rescue request is placed into the order based on the battery life of the respective computing device, an estimated arrival time of an emergency responder assigned to the respective rescue request, and the one or more geofencing factors,
        identify the emergency responder to dispatch to each respective victim based at least in part on the generated order, and
        coordinate dispatch of the emergency responder based on the emergency information; and
    a second computing device comprising one or more third processors programmed to execute instructions that cause at least one third processor of the one or more third processors to receive dispatch instructions from the at least one server, the dispatch instructions including the emergency information and a location of the first computing device.

2. The emergency response system of claim 1, wherein the first rescue request packet comprises one of a text-to-911 message, a communication from a rescue application operating on the first computing device, a received image or video file, or data scraped from one or more social media posts or communications.

3. The emergency response system of claim 2, wherein the rescue application collects the emergency information via a dynamic user interface by at least:
    presenting a first user interface providing user-selectable options that enable the user to select an emergency type from among a plurality of emergency types;
    receiving an indication of user selection of one of the user-selectable options, the one of the user-selectable options associated with the emergency type; and
    based on the indication of the user selection, presenting at least one follow-up user interface that enables the user to provide the emergency information, wherein the at least one follow-up user interface relates specifically to the emergency type.

4. The emergency response system of claim 3, wherein the rescue application generates one or both of the first user interface and the at least one follow-up user interface based at least partly on real-time disaster tracking.

5. The emergency response system of claim 3, wherein:
    the rescue application displays, in the at least one follow-up user interface, at least one selectable option associated with an emergency severity point value;
    the rescue application calculates an emergency severity score based on the user selecting the at least one selectable option and the associated emergency severity point value; and
    wherein the server performs automated triaging of each of the rescue requests based at least partly on the emergency severity score.

6. The emergency response system of claim 2, wherein the rescue application:
    performs analysis of a signal strength of a cellular Internet network and a volume of communications being handled by the cellular Internet network; and
    based on a result of the analysis, causes the first computing device to transmit the first rescue request packet to the at least one server via either the cellular Internet network or SMS.

7. The emergency response system of claim 2, wherein, after receipt of the dispatch instructions by the responder application, the rescue application provides at least one update to the second computing device regarding the location of the first computing device.

8. The emergency response system of claim 1, wherein the server performs automated triaging of the first rescue request packet based at least partly on a user severity score calculated based on the emergency information and on a distance between the location of the first computing device and a nearest responder hub.

9. The emergency response system of claim 1, wherein the server is further configured to determine a confidence level for the rescue request from each of the plurality of rescue request packets and triage the rescue requests based at least in part on the confidence level for each of the rescue request as compared to each other.

10. A computer-implemented method, comprising:
receiving a plurality of rescue request packets from a plurality of computer devices, including a first rescue request packet based on emergency information provided by a user from a first computing device;
receiving one or more geofencing factors from at least one of the plurality of rescue request packets;
identifying a plurality of rescue requests from the plurality of rescue request packets, each rescue request corresponding to one of the rescue request packets and providing details regarding a respective victim, respective emergency conditions based on respective emergency information, and respective computing device information including a battery life of a respective computing device;
triaging each of the rescue requests to generate an order according to which the respective victims are to be rescued, wherein each rescue request is placed into the order based on the battery life of the respective computing device, an estimated arrival time of an emergency responder assigned to the respective rescue request, and the one or more geofencing factors;
identifying the emergency responder to dispatch to each respective victim based at least in part on the generated order;
coordinating dispatch of the emergency responder based on the emergency information; and
transmitting dispatch instructions to the emergency responder, the dispatch instructions including the emergency information and a location of the first computing device.

11. The computer-implemented method of claim 10, wherein the first rescue request packet comprises one of a text-to-911 message, a communication from a rescue application operating on the first computing device, a received image or video file, or data scraped from one or more social media posts or communications.

12. The computer-implemented method of claim 10, further comprising:
collects the emergency information via a dynamic user interface by at least:
presenting a first user interface providing user-selectable options that enable the user to select an emergency type from among a plurality of emergency types;
receiving an indication of user selection of one of the user-selectable options, the one of the user-selectable options associated with the emergency type;
based on the indication of the user selection, identifying at least one follow-up user interface that enables the user to provide emergency information relating specifically to the emergency type;
presenting the at least one follow-up user interface to the user;
collecting the emergency information from the user based on interaction between the user and the at least one follow-up user interface; and
transmitting a rescue request packet including the emergency information to the emergency response system.

13. The computer-implemented method of claim 12, further comprising displaying, in the at least one follow-up user interface, at least one selectable option that collects emergency severity information from the user.

14. The computer-implemented method of claim 10, wherein the rescue request packet includes the location of the user computing device, the method further comprising identifying the location via a global positioning system.

15. The computer-implemented method of claim 14, further comprising:
after receiving the rescue request packet, transmitting an indication that an emergency responder has been dispatched to the location of the user computing device; and
providing at least one update regarding the location of the user computing device to a designated computing device of the emergency responder.

16. The computer-implemented method of claim 15, wherein providing the at least one update includes determining whether to preserve the battery life of the user computing device or to ping the global positioning system for the at least one update, the method further comprising, in response to determining to preserve the battery life, providing a last known location of the user computing device.

17. The computer-implemented method of claim 16, further comprising, in response to determining to ping the global positioning system:
receiving an update to the location of the user computing device from the global positioning system; and
sending the update to the designated computing device of the emergency responder.

18. The computer-implemented method of claim 10, further comprising identifying whether to use a cellular Internet network or SMS to transmit the rescue request packet based on analyzing a signal strength of the cellular Internet network and a volume of communications of the cellular Internet network.

19. Non-transitory, computer-readable storage media storing computer-executable instructions that, when executed by a computer system, configure the computer system to perform operations comprising:
receiving a plurality of rescue request packets from a plurality of computer devices, including a first rescue request packet based on emergency information provided by a user from a first computing device;
receiving one or more geofencing factors from at least one of the plurality of rescue request packets;
identifying a plurality of rescue requests from the plurality of rescue request packets, each rescue request corresponding to one of the rescue request packets and providing details regarding a respective victim, respective emergency conditions based on respective emergency information, and respective computing device information including a battery life of a respective computing device;
triaging the rescue requests to generate an order according to which the respective victims are to be rescued, wherein each rescue request is placed into the order based on the battery life of the respective computing device, an estimated arrival time of an emergency responder assigned to the respective rescue request, and the one or more geofencing factors;
identifying the emergency responder to dispatch to each respective victim based at least in part on the generated order;
coordinating dispatch of the emergency responder based on the emergency information; and
transmitting dispatch instructions to the emergency responder, the dispatch instructions including the emergency information and a location of the first computing device.

20. The non-transitory, computer-readable storage media of claim 19, wherein the first rescue request packet comprises one of a text-to-911 message, a communication from a rescue application operating on the first computing device, a received image or video file, or data scraped from one or more social media posts or communications.

\* \* \* \* \*